US006958061B2

(12) United States Patent
Truckai et al.

(10) Patent No.: US 6,958,061 B2
(45) Date of Patent: Oct. 25, 2005

(54) MICROSPHERES WITH SACRIFICIAL COATINGS FOR VASO-OCCLUSIVE SYSTEMS

(76) Inventors: Csaba Truckai, 19566 Arden Ct., Saratoga, CA (US) 95070; John H. Shadduck, 1490 Vistazo West, Tiburon, CA (US) 94920

( * ) Notice: Subject to any disclaimer, the term of this patent is extended or adjusted under 35 U.S.C. 154(b) by 218 days.

(21) Appl. No.: 10/456,149

(22) Filed: Jun. 5, 2003

(65) Prior Publication Data

US 2003/0212427 A1 Nov. 13, 2003

Related U.S. Application Data

(60) Provisional application No. 60/386,544, filed on Jun. 5, 2002.

(51) Int. Cl.[7] .............................................. A61B 18/18
(52) U.S. Cl. ........................... 606/28; 606/213; 606/41
(58) Field of Search ............................. 606/27–31, 41, 606/48–50, 213–216

(56) References Cited

U.S. PATENT DOCUMENTS

| 6,033,401 A | * | 3/2000 | Edwards et al. ............... 606/41 |
| 6,179,862 B1 | * | 1/2001 | Sawhney ..................... 606/214 |
| 6,511,477 B2 | * | 1/2003 | Altman et al. ................ 606/41 |

* cited by examiner

Primary Examiner—Michael Peffley
(74) Attorney, Agent, or Firm—Townsend and Townsend and Crew LLP

(57) ABSTRACT

A vaso-occlusive system comprising a catheter with a working end that carries a fluid media for introduction into an aneurysm. The fluid media carries a volume of microspheres, wherein each microsphere has a sacrificial shell or coating that surrounds an interior core portion of the microsphere. The core portions of the microspheres comprise either a first or second polymerizing composition, wherein interaction of such binary compositions will cause polymerization of the media into a gel or solid media that will occlude the aneurysm. An energy delivery means is provided within the catheter working end to cause removal of the sacrificial coatings of the volume of microspheres to thereby induce the polymerization process.

20 Claims, 24 Drawing Sheets

MICROSPHERES WITH SACRIFICIAL COATINGS FOR VASO-OCCLUSIVE SYSTEMS

CROSS-REFERENCE TO RELATED APPLICATION

This application claims the benefit of Provisional U.S. patent application Ser. No. 60/386,544 filed Jun. 5, 2002, having the same title, which application is incorporated hereby by this reference.

FIELD OF THE INVENTION

This invention relates to medical systems and techniques for occluding aneurysms. More particularly, the vaso-occlusive provides a fluid media for introduction into an aneurysm that consists of a binary system of microspheres. Each microsphere has a sacrificial coating that surrounds an interior core of the microsphere. The cores of the microspheres comprise either a first or second polymerizing composition, wherein interaction of such binary compositions will cause polymerization of the media into a gel or solid media that to occlude the aneurysm. An energy source is carried at the catheter working end to cause removal of the sacrificial coatings of the microspheres to induce the polymerization process.

BACKGROUND OF THE INVENTION

Various devices and techniques have been developed for occluding aneurysms or other vascular defects or deformations (herein termed malformations). A common type of aneurysm treatment utilizes a detachable coil that is fed into the aneurysm to substantially occupy the aneurysm volume. The typical approach for implanting an embolic coil in an aneurysm involves attaching the coil to the distal end of a pushwire, and introducing the pushwire and coil through a catheter lumen until the coil is pushed into the aneurysm. The typical manner of detaching the coil from the pushwire involves using a direct current to cause electrolysis of a sacrificial joint between the pushwire and the coil. The coil can then serve to mechanically occlude a significant volume of the aneurysm and thereby reduce blood circulation within the aneurysm. After a period of time ranging from several hours to several weeks, the volume of the aneurysm can become fully occluded as blood clots about the coil. Eventually, the aneurysm will be reduced and reabsorbed by the body's natural wound healing process. This type of vaso-occlusion system was disclosed by Gugliemli in U.S. Pat. Nos. 5,122,136 and 5,354,295.

Another manner of treating an aneurysm was disclosed by Gugliemli (see U.S. Pat. Nos. 5,976,131; 5,851,206) and is described as electrothrombosis. In this particular approach, a catheter and pushwire are used to push a wire coil into the aneurysm that is connected to an electrical source. The system then delivers radio frequency (Rf) current to the coil which is adapted to heat the blood volume within the aneurysm to cause thermal formation of thrombus (see U.S. Pat. No. 5,851,206; Col. 5, line 5). The conductive coil disclosed by Guglielmi in U.S. Pat. No. 5,976,131 has an insulated tip or other arrangements of insulation around the coil to prevent localized "hot spots" (see U.S. Pat. No. 5,976,131; Col. 3, line 53).

It is believed that several risk factors are involved in any uncontrolled use of significant levels of Rf energy to cause so-called electrothrombosis. Most important, the use of electrical energy to cause current flow between a coil (first electrode) within an aneurysm and a ground (a second body electrode) will likely cause high energy densities and highly localized heating of tissue that comes into contact with the coil. If the wall of the aneurysm contacts the energized portion of a coil, there is a significant danger of perforation or ablation of the aneurysm wall that could be life-threatening. Further, the use of uncontrolled energy delivery to an implanted coil could heat adjacent brain tissue to excessive levels resulting in loss of brain function or even death. For these reasons, the coils disclosed by Gugliemli were provided with an insulating material covering the tip of the coil that is most likely to come into contact the wall of the aneurysm. However, it is still likely that unwanted localized heating will occur within the aneurysm sac when attempting to cause ohmic heating of the blood volume in an aneurysm by creating Rf current flow between an electrode coil and a body electrode.

Another disadvantage of using the typical commercially available wire coil is that the physician must estimate dimensions and volume of the aneurysm and then feed multiple coils into the aneurysm. The deployment of each coil is time consuming, and the detachment of the coil from the introducer pushwire also is time consuming.

SUMMARY OF THE INVENTION

In general, this invention comprises a vascular occlusion system for treating aneurysms that provides a novel class of continuous extruded polymer embolic elements that carry thin metallic or conductive coatings that provide a specified resistivity to electrical current flow. Alternatively, the polymer element is fabricated with such specified resistivity by providing conductive microfilaments or conductive particles embedded within an extruded polymer element. The embolic element is introduced into a targeted site in a patient's vasculature by a microcatheter sleeve. The thin metallic coating allows the embolic element to be soft and flexible, and more importantly, allows the physician to select any desired length (and volume) of embolic element in vivo for causing mechanical occlusion of the aneurysm. The system of the invention also provides an electrical source and computer controller for feedback modulation of power delivery with a first (low) range and a second (high) range to accomplish two different methods of the invention. The electrical source is coupled to an electrode arrangement at the distal terminus of the catheter sleeve that contacts the surface of the embolic element as it is slidably deployed from the catheter. Thus, energy is delivered to the resistive layer of the embolic element directly from the distal terminus of the catheter sleeve. The catheter working end also carries a thermocouple, coupled to feedback circuitry, for sensing the temperature of the deployed embolic element and controlling its temperature via power modulation. The embolic element can be fabricated with a resistive metallic component to cooperate with single electrode have a single polarity at the catheter working end. Alternatively, the embolic element can be fabricated with spaced apart metallic surface portions to cooperate with bi-polar electrodes at the catheter working end.

In a method of using an exemplary system, the physician pushes the embolic element from the distal terminus of a catheter into a targeted site in a patient's vasculature thereby mechanically occluding a selected volume of the aneurysm or other vascular malformation. After disposing a selected length of the embolic element within the targeted site, the physician then actuates the electrical source via the controller to deliver electrical current within a first (low) power range to the conductive component of the polymer element from the electrode at the catheter's distal terminus. The electrical energy delivery to the metallic component that provides the specified resistivity (e.g., preferably ranging between about 0.5 ohms and 25 ohms/cm. of embolic element) causes resistive heating of the surface of the deployed embolic element over a particular calculated length of the element that extends distally from the electrode. This thermal effect causes denaturation of blood components that results in the formation of layer of coagulum about the deployed embolic element. Additionally, the current flow within this first range causes active or ohmic heating of blood proximate to the embolic element in a manner that facilitates the formation of the coagulative layer about the embolic element. During energy delivery, the temperature sensor at the catheter working end sends signals to the controller that are used to modulate power delivery to maintain the embolic element at, or within, a particular temperature or range at the catheter's distal terminus. By this manner of operation, the system can controllably create a selected thickness of coagulum about the surface of the embolic element. Thus, the initial deployment of the selected length of the embolic element mechanically occludes or occupies a selected (first) volume of a vascular malformation. Thereafter, controlled energy delivery thermally induces a layer of coagulative to form, thereby providing another selected volume of material to occlude or occupy a selected (second) volume of the vascular malformation. These methods of the invention provide means to cause rapid mechanical occlusion of blood flow within the malformation while preventing any significant energy densities in the targeted site.

In the next manner of practicing a method of the invention, the physician directs the controller and electrical source to deliver current at a second (higher) power level to the metallic component of the embolic element from the same electrode arrangement at the catheter's distal end. This second power level causes the metallic component together with the polymer core of the embolic element to act like a fuse at the catheter sleeve's terminus. This selected power level, within a fraction of a second, can thermally melt or divide the deployed portion of the continuous polymer embolic element from the remainder of the element still within the catheter sleeve. This aspect of the method of the invention allows the physician to select any length of embolic element intra-operatively under fluoroscopy, which is not possible in the prior art.

The invention advantageously provides a system and method for intra-operatively disposing any selected length and selected volume of an occlusive element in a targeted site in a patient's vasculature to mechanically occlude a malformation.

The invention provides a system and method that does not require the physician to pre-select a particular length of a coil element for implantation in an aneurysm.

The invention provides a system and method that does not require the physician to deploy multiple separate coil elements in separate sub-procedures to occlude an aneurysm.

The invention advantageously provides a system and method that utilizes a polymer embolic member that carries a metallic component with a specified resistivity to current flow to thereby allow controlled energy delivery within, and about, the member to create a pre-determined thickness of coagulum about the embolic member for mechanically occluding a vascular malformation.

The invention provides a system with feedback control that modulates power delivery from a source to an embolic element to maintain the embolic element at a specified temperature or within a specified temperature range.

The invention provides a system with feedback control that modulates power delivery to create a pre-selected thickness and volume of occlusive material about an embolic element.

The invention provides a self-terminating electrical energy delivery modality for creating a layer of occlusive material about an embolic element.

The invention advantageously provides a system and method that allows the delivery of electrical energy to an embolic element within an aneurysm without the risk of localized high energy densities.

The invention advantageously provides a system and method that delivers electrical energy to an embolic element to increase the volume of occlusive material in an aneurysm while eliminating the risk of perforating the wall of the aneurysm.

The invention provides a system and method that delivers electrical energy to an embolic element to increase the volume of occlusive material in a cerebral aneurysm while preventing collateral thermal damage to brain structure.

The invention provides an embolic member with a specified resistivity by fabricating the a polymer member with at least one very thin conductive surface layer.

The invention provides an embolic member with a specified resistivity by fabricating the polymer extrusion with conductive microfilaments embedded therein.

The invention provides an embolic member with a specified resistivity by extruding a polymer matrix with conductive particles embedded therein.

The invention advantageously provides a system and method utilizes a polymeric element with first and second portions of a metallic cladding that is adapted to serve as a bi-polar electrode arrangement for creating a coagulative layer.

The invention provides a method for controllably creating a coagulative volume about an embolic member by (i) controlling the center-to-center distance between spaced apart conductive components of the embolic member, and (ii) controlling the rate of energy delivery between the spaced apart conductive portions.

BRIEF DESCRIPTION OF THE DRAWINGS

Other objects and advantages of the present invention will be understood by reference to the following detailed description of the invention when considered in combination with the accompanying Figures, in which like reference numerals are used to identify like components throughout this disclosure.

FIGS. 14A–14C are illustrations of the method of practicing the invention, wherein:

FIG. 14A depicts the mesh-like polymer sleeve carries in a non-expanded position at the working end of a catheter;

FIG. 14B depicts expansion of the mesh-like polymer sleeve by expansion means comprising at least one balloon; and FIG. 14C depicts the mesh-like polymer sleeve fused to the vessel wall across the vascular malformation after delivery of electrical energy to the filaments.

DETAILED DESCRIPTION OF THE INVENTION

Figure 1:
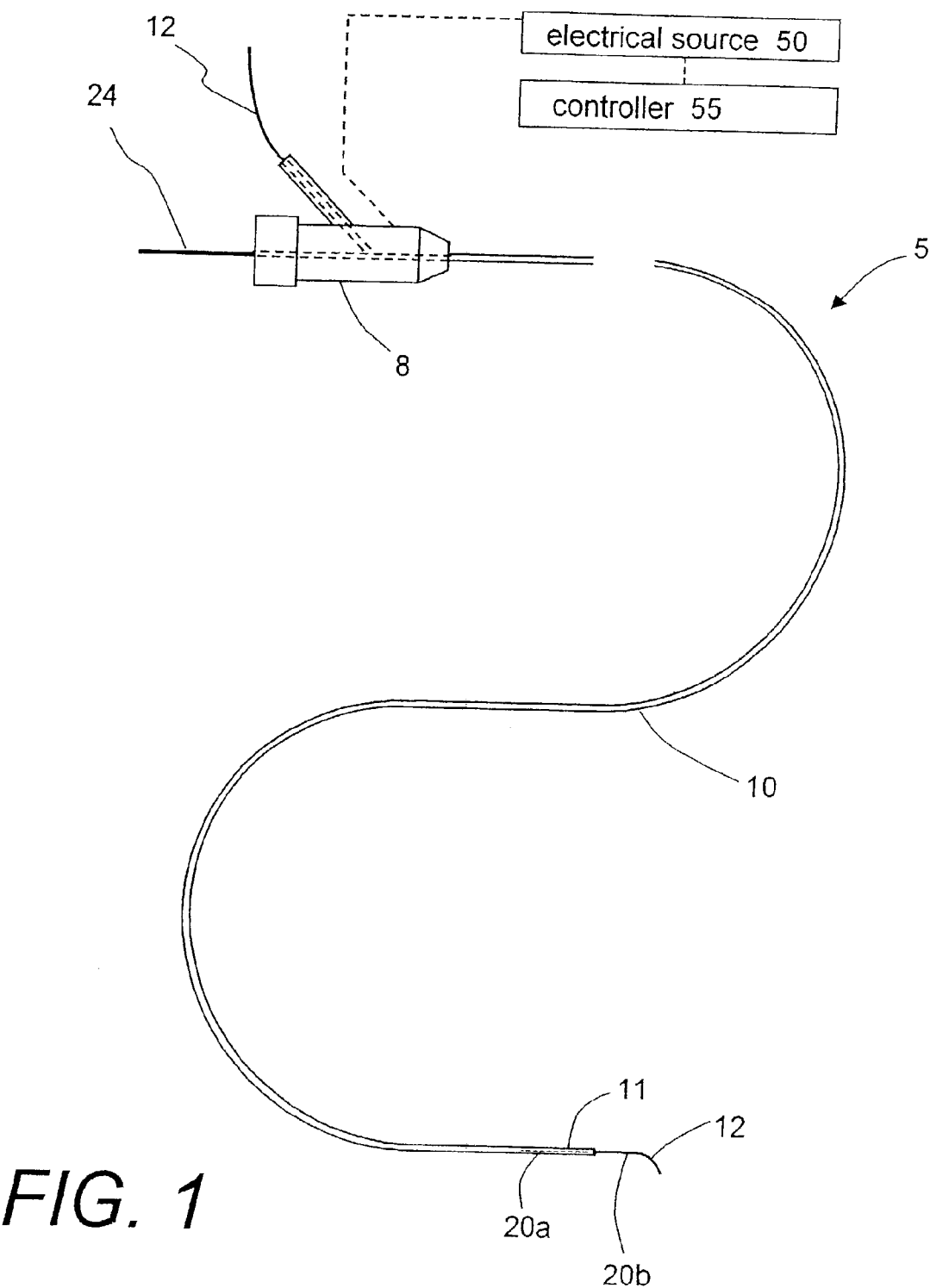
FIG. 1 shows a plan view of Type "A" vaso-occlusive system with an elongate catheter sleeve that carries the polymer embolic element made in accordance with the principles of the present invention.
Figure 2:
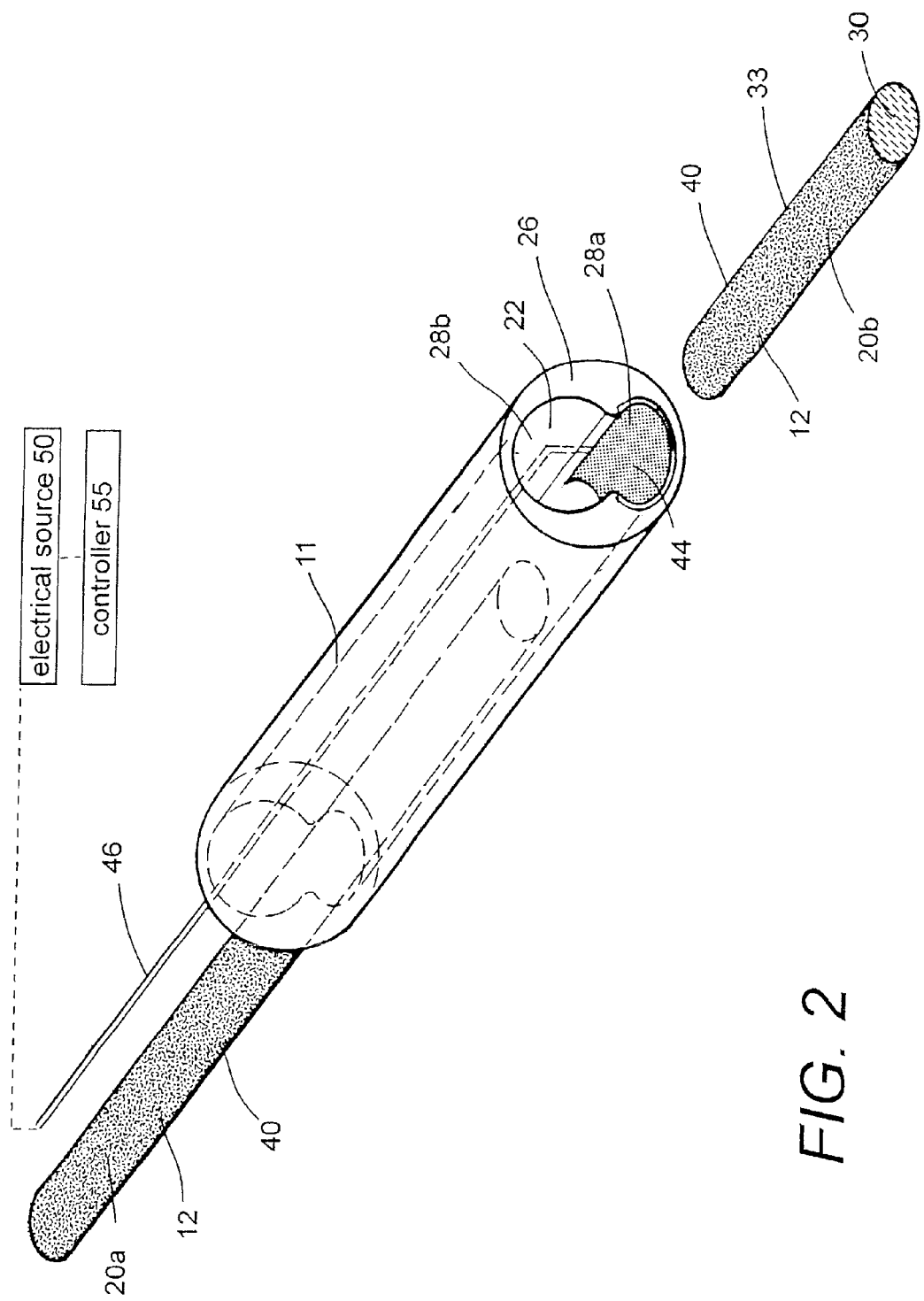
FIG. 2 is an enlarged cut-away view of the working end of the catheter sleeve of FIG. 1 showing an exemplary polymer embolic element with a metallic coating and an electrode arrangement carried within the catheter sleeve.

1. Type "A" embodiment of vascular occlusive system. FIG. 1 shows an elevational view of a Type "A" catheter system 5 for occluding an aneurysm or other vascular malformation. The catheter system has a proximal handle or manifold 8 as is known in the art that is coupled to an elongate microcatheter sleeve 10. FIG. 2 is a cut-away view of the working end 11 of catheter sleeve 10 that illustrates the metallic-coated elongate thread or filament element 12 corresponding to present invention that can be passed axially through the cooperating microcatheter sleeve 10. The flexible embolic element 12 defines a proximal portion 20a still carried within catheter sleeve 10 and a distal thread portion 20b that is pushed outward of the catheter. In this exemplary embodiment, the embolic element 12 has an oval or flattened cross-section, but other cross-sectional shapes are suitable.

Figure 3:
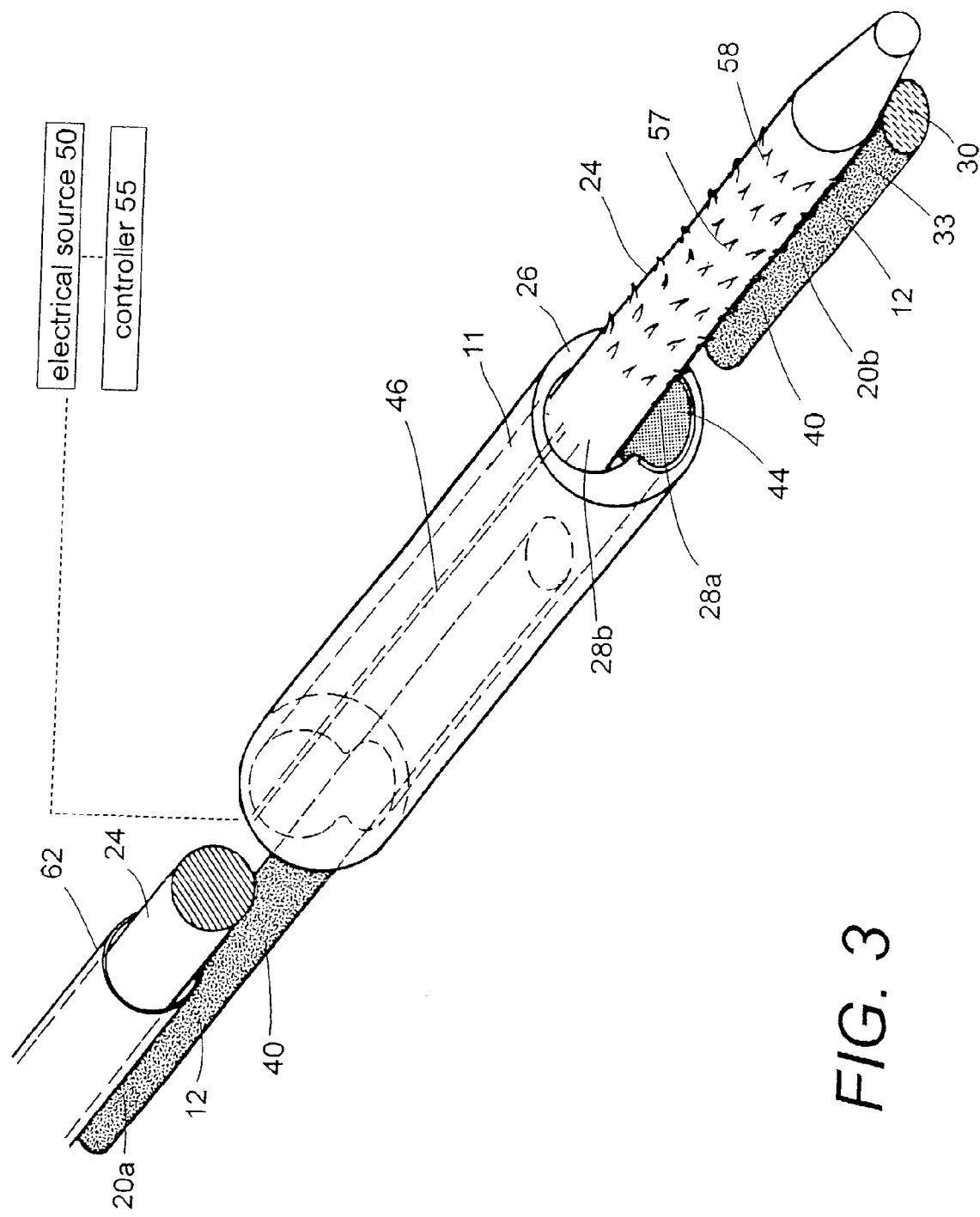
FIG. 3 is a cut-away view of the working end of FIG. 2 with an exemplary extension member adapted for pushing the polymer embolic element member distally from the catheter sleeve.
Figure 4:
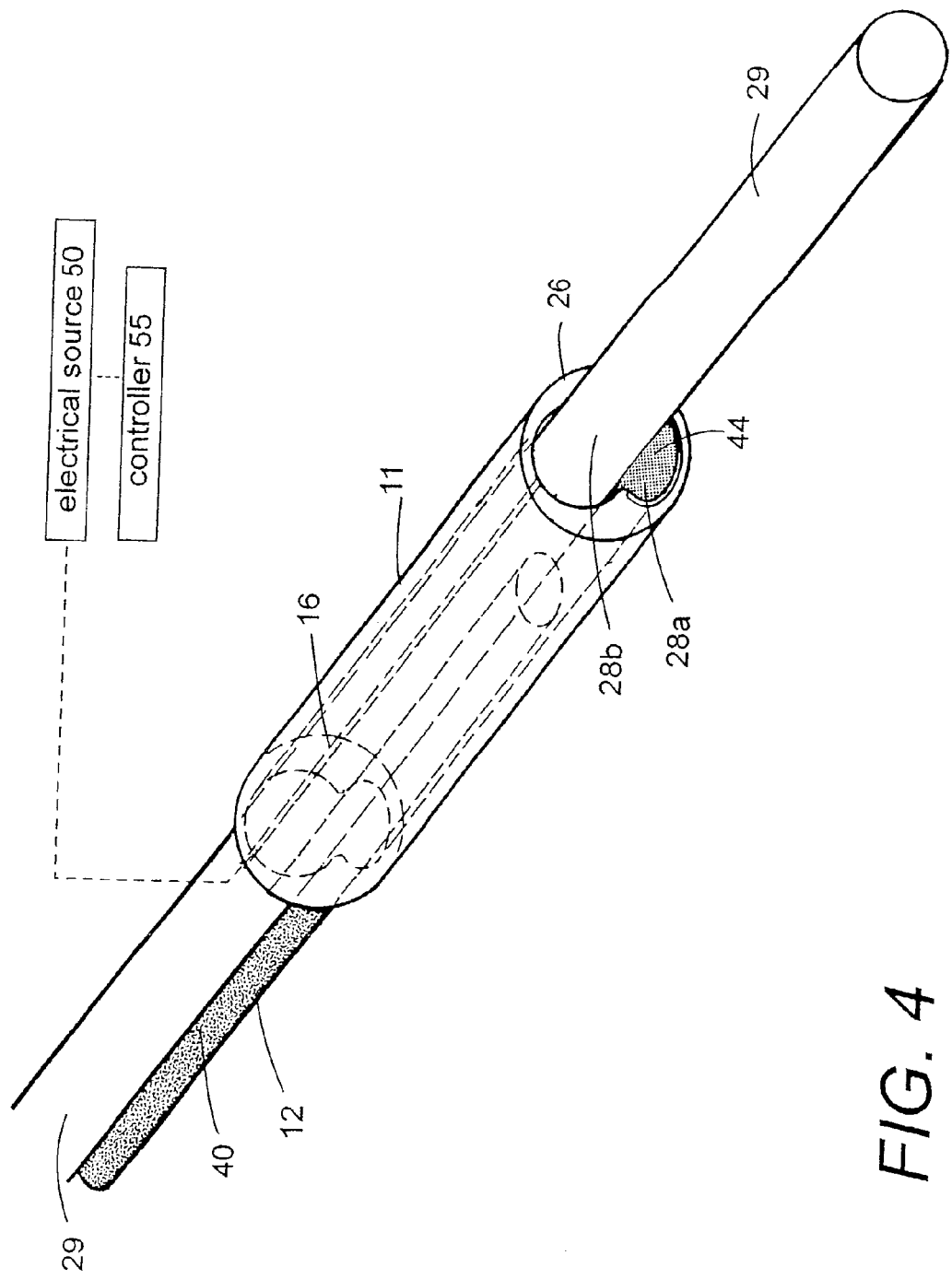
FIG. 4 shows the manner in which the working end of FIG. 2 can be introduced over a guidewire.
Figure 5A:
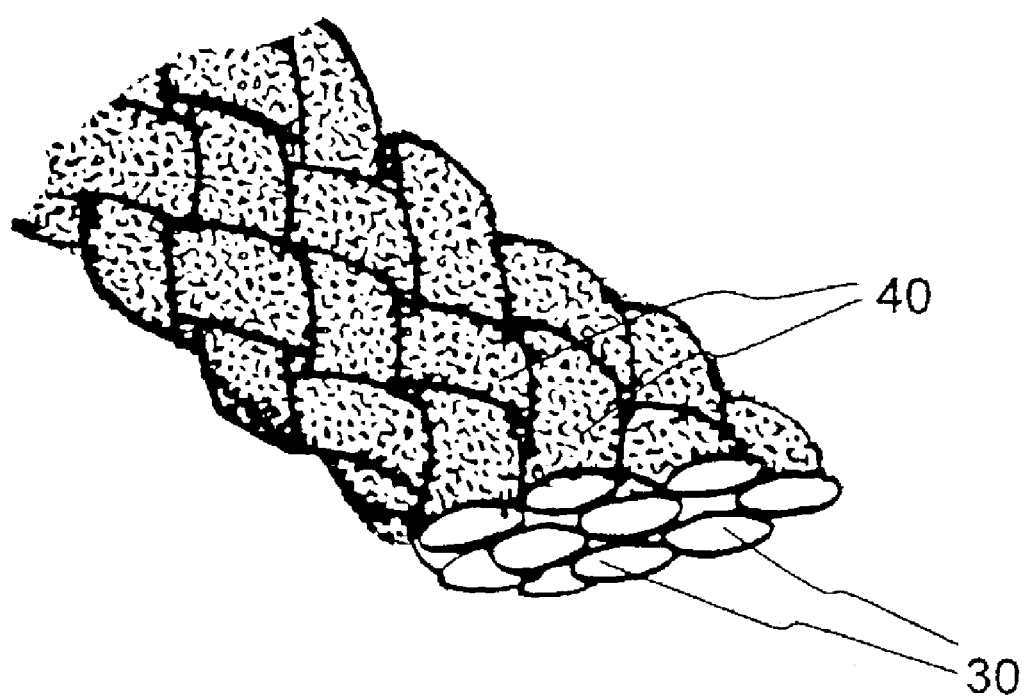
FIG. 5A is view of view of a portion of an alternative embolic element made up of multiple metallic coated filaments.
Figure 5B:
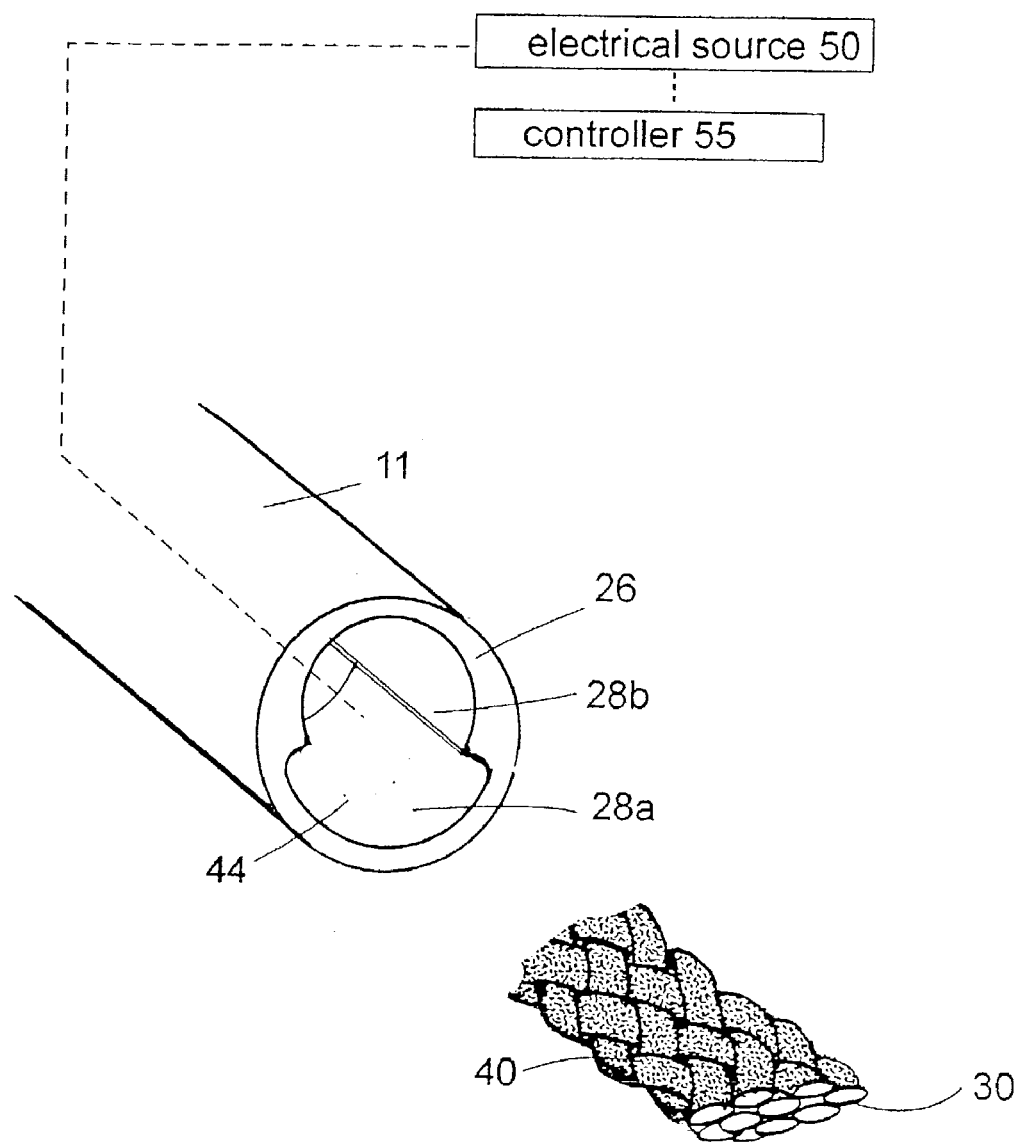
FIG. 5B is a view of the passageway in an alternative embodiment of catheter sleeve that cooperates with embolic element of FIG. 5A.

In this exemplary embodiment, an internal bore or passageway 22 within the catheter sleeve 10 is adapted to carry the embolic thread element 12 as well as to receive a slidable extension member 24 for pushing the polymer thread element 12 from the distal termination 26 of the catheter (see FIG. 3). As can be seen in FIGS. 2 & 3, the cross-sectional form of passageway 22 in the catheter sleeve has a first oval-shape bore portion indicated at 28a for carrying the polymer thread element 12 and a second round-shape bore portion indicated at 28b for slidably receiving the round extension member 24. The second bore portion 28b also is adapted for sliding over a guidewire 29 as shown in FIG. 4. It should be appreciated that the embolic element 12 and cooperating passageway 22 in the catheter sleeve 10 can be formed in several cross-sectional shapes and configurations (e.g., round, flattened and flexible, braided, etc.) and is shown in FIGS. 5A–5B with the embolic element comprising a flattened braid of polymer microfilaments. The cooperating extension member 24 may have and suitable type of mechanism for pushing, pulling, helically advancing, or otherwise expelling the embolic element 12 from distal termination 26 of the catheter sleeve.

Referring now to FIGS. 1 & 2, it is possible to describe several features and characteristics of embolic thread element 12 that adapt it for use in occluding an aneurysm sac or any other vascular malformation. The embolic element 12 has a core 30 of a continuous length of a flexible biocompatible polymeric material, such as nylon, PET, polyamide, aramid fiber, urethane or Kevlar®. The total length of the embolic element or member 12 may range from about 40 cm. to 2000 cm. The cross-sectional dimension of embolic element 12 may range from about 0.0005" to 0.030" in a round cross-section element, or similar cross-sectional area in any rectangular or other sectional shape. A suitable polymer material can be fabricated in an extrusion process, for example, by Polymicro Technologies LLC, 18019 N. 25th Ave., Phoenix, Ariz. 85023-1200. The polymer embolic element 12 further carries a radio-opaque composition as in known in the art (e.g., $BaSO_4$, $BiO_3$) to allow fluoroscopic viewing of embolic element 12 as it is maneuvered within a patient's vasculature. The core 30 of the embolic element 12 preferably (but optionally) is somewhat porous thus resulting in an irregular surface indicated at 33 to improve the gripping surface of thin-layer conductive or metallic coating 40 on the embolic element as is described next. FIGS. 5A-5B show an embolic element 12 comprising a plurality of small diameter filaments 42 woven into a flexible braid, with each filament having a metallic coating as described below. A braided embolic element 12 such as depicted in FIG. 5A also would provide a suitable surface 33 for gripping with extension member 24 as described below. It should be appreciated that the flexible embolic element may have a curved or coiled repose shape, and then be straightened as it is passed through the catheter sleeve. Upon deployment, the embolic element would again assume its repose coiled shape to facilitate its introduction into an aneurysm.

As can be seen in FIG. 2, the embolic element 12 carries a thin-layer conductive or metallic coating 40 that has a selected electrical resistivity for accomplishing a method of the invention described below. The metallic coating 40 may be any suitable biocompatible material that can be formed in, or deposited on, the elongate polymeric element 12, such as gold, platinum, silver, palladium, tin, titanium, tantalum, copper or combinations or alloys of such metals, or varied layers of such materials. A preferred manner of depositing a metallic coating 40 on the polymer element comprises an electroless plating process known in the art, such as provided by Micro Plating, Inc., 8110 Hawthorne Dr., Erie, Pa. 16509-4654. The preferred thickness of the metallic coating ranges between about 0.00001" to 0.005". More preferably, the coating thickness ranges between about 0.0001" to 0.001". Still more preferably, the thickness of the conductive coating ranges between about 0.0005" to 0.0007". As will be described below in the Type "C" embodiment, the polymer element also may be extruded with conductive filaments or particles embedded within the polymer matrix of core 30 of the element.

Of particular interest, the combination of the core 30 and metallic or conductive coating 40 of the embolic element 12 provides a selected resistivity to current flow that ranges from about 1 ohm to 500 ohms per 10 cm. length of the embolic element 12 to cause controllable heating about the surface 33 of embolic element 12. More preferably, the element provides a resistivity ranging between about 5 ohms to 250 ohms per 10 cm. length. Still more preferably, the core 30 and conductive coating 40 provide a selected resistivity ranging between about 30 ohms to 60 ohms per 10 cm. length of the embolic element 12.

FIGS. 2 & 3 further illustrate that the distal end of catheter sleeve 10 carries a conductive electrode surface indicated at 44 about a distal region of bore portion 28a that carries embolic element 12. The electrode 44 is coupled to electrical lead 46 that extends within the wall 48 of the catheter to its proximal handle end and to electrical source 50 and controller 55. It should be appreciated that the electrical lead 46 can be a part of a helical braid reinforcement within the catheter sleeve. As can be easily understood by viewings FIGS. 2 & 3, the elongate embolic element 12 can be pushed distally from bore portion 28a, and no matter the axial position of the embolic element, and electrode 44 will substantially contact the metallic surface 40 of the polymer element 12. As will be described below in the method of the invention, the electrical source 50 and electrode arrangement of catheter 10 in combination with the metallic coating of the polymer element 12 are adapted to (i) facilitate rapid occlusion of an aneurysm, and (ii) to sever or divide the polymer thread element 12 to thereby implant any selected length of distal portion 20b of polymer element 12 within in the aneurysm while retaining a proximal length 20a of the polymer element in bore 28a of the catheter. As shown in FIG. 3, the electrode 44 is shown for convenience at the distal end of the catheter sleeve. Preferably, the electrode 44 is spaced slightly inward or proximal from the distal termination 26 of the sleeve to prevent any substantial electrode surface from being exposed to the blood volume proximate to a targeted treatment site.

Figure 5C:
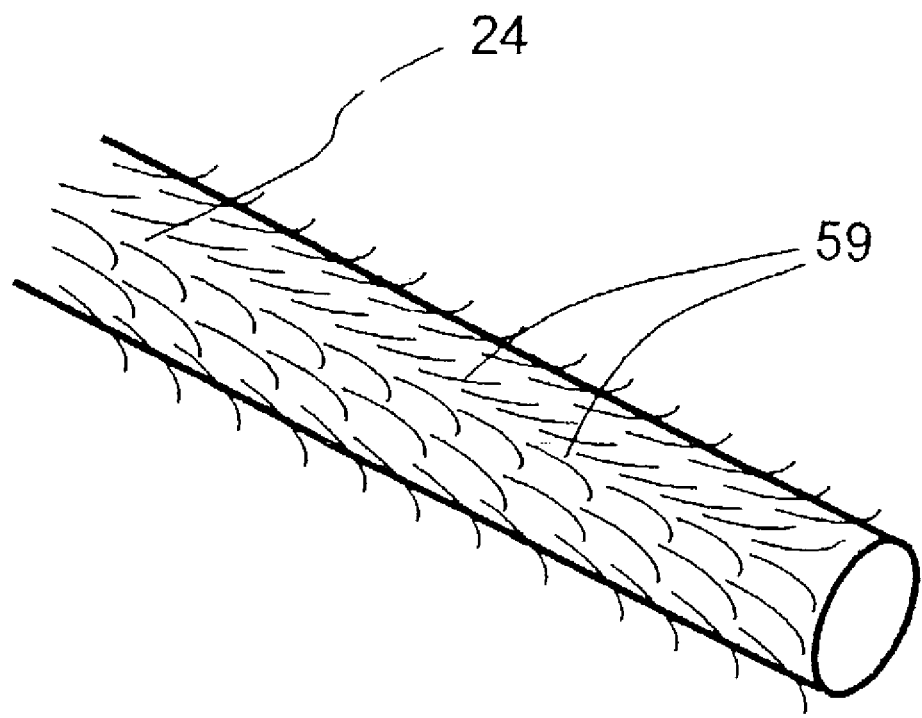
FIG. 5C is a perspective view of an alternative embodiment of extension member adapted to grip the embolic element.

In the system shown in FIGS. 2 & 3, the exemplary polymer element 12 is very soft and flexible, for example, having the flexibility characteristics of a common thread or suture. In order to deploy the polymer thread element 12 from distal termination 26 of catheter sleeve 10, this embodiment utilizes a slidable extension member 24 that has unidirectional gripping elements 57 (herein alternatively called barbs) about a distal region 58 of the extension member 24. As can be understood in viewing FIG. 2, an axial movement or projection of extension member 24 from sleeve 10 will cause the barb elements 57 to grip the embolic element and pull it from bore portion 28a. When the extension member 24 is moved proximally in bore portion 28b, the barb elements will slide over surface 33 of embolic element 12 thus leaving a selected length of the embolic element disposed outside distal termination 26 of the catheter sleeve. The barb or gripping elements 57 may be provided in extension member 24 may comprise cuts into the surface of a polymer extension member 24. Alternatively, the gripping elements may comprise a fiber or other type of hair-like filament 59 bonded to the surface of an extension member 24 as shown in FIG. 5C.

The catheter sleeve 10 while carrying the polymer embolic element in bore portion 28a may be introduced into vasculature over a guidewire 29 as shown in FIG. 4. The guidewire then can be removed and be replaced by the extension member 24. To facilitate the slidable introduction of the extension member 24 and grip elements into bore portion 28b while embolic element 12 is carried within bore portion 28a, the extension member may cooperate with a very thin-wall sleeve 62 of Teflon® or any other suitable material to prevent the gripping elements 57 from gripping the embolic element 12 as the guidewire is replaced with the extension member 24. As can easily understood from viewing FIG. 3, to expose the distal portion 58 of the extension member 24 and gripping elements 57, the thin-wall sleeve 62 can be retracted from the gripping elements by pulling it proximally at the handle 8 of the catheter.

The system 5 further provides feedback control mechanisms within controller 55 for modulating energy delivery to electrode 44 and thereby to the conductive component of the embolic element. Referring again to FIG. 3, at least one thermocouple 88 is provided at either surface of electrode 44 to measure the temperature of the electrode which is substantially the same as the surface temperature of the embolic element in contact therewith. The thermocouple 88 is linked to controller 55 by an electrical lead (not shown). The controller 55 is provided with software and algorithms that are adapted to modulate power delivery from electrical source 50 to maintain the temperature of the embolic element (or electrode 44) at a particular level or within a particular temperature range, in response to feedback from the sensor.

Figure 6A:
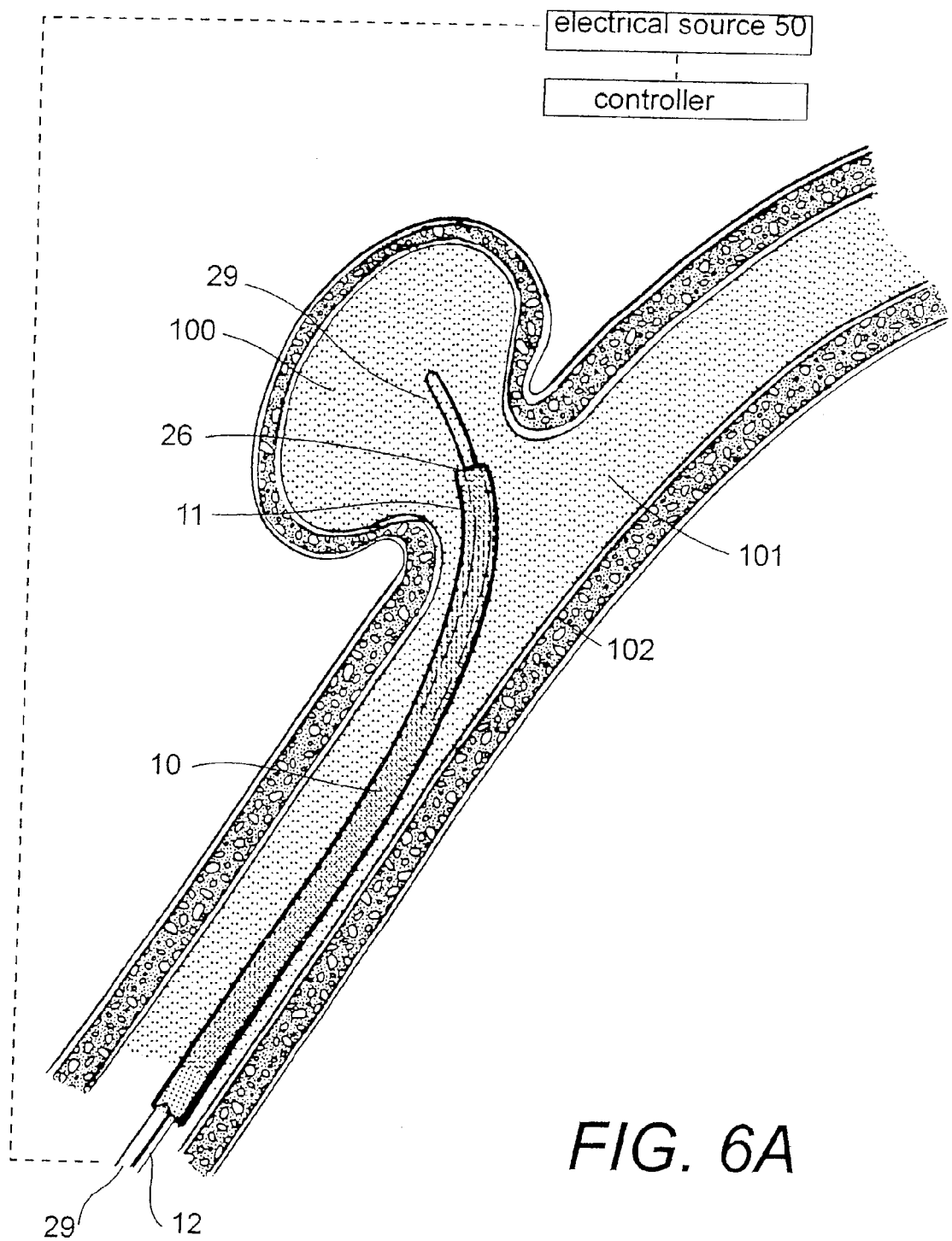
FIG. 6A is a view of the working end of the Type "A" system of FIGS. 1 & 2 disposed in a blood vessel proximate to an aneurysm.
Figure 6B:
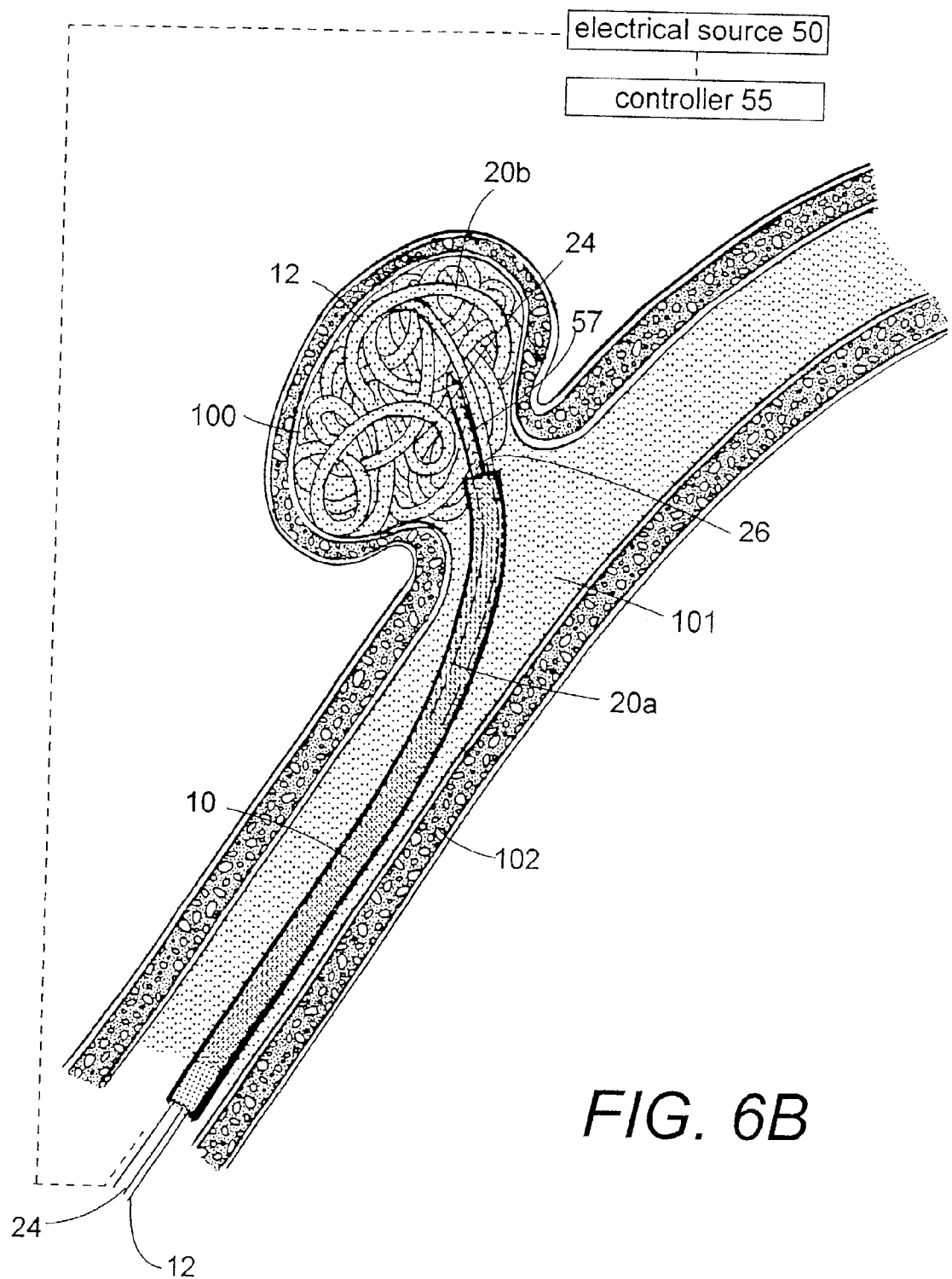
FIG. 6B is a view of the working end of FIG. 6A after a selected length of a distal portion of the polymeric member is disposed in the aneurysm and formed into a tangled mass to occupy a volume of the aneurysm.

Now turning to FIGS. 6A–6B, the manner of using the catheter system 5 to introduce the polymer embolic element 12 into a cerebral aneurysm indicated at 100 or any other targeted vascular site is shown. In FIG. 6A, it can be seen that working end 11 of catheter sleeve 10 is introduced through blood 101 flowing in vessel 102 until its distal termination 26 is positioned adjacent to, or partially within, the aneurysm 100. Typically, the catheter is guided to the aneurysm over guidewire 29 that is accommodated by bore portion 28b of the catheter sleeve (see FIGS. 4 & 6A). In FIG. 6B, it can be seen that guidewire 29 has been withdrawn from catheter passageway 28b, and thereafter the extension member 24 has been introduced back through the same passageway. The (optional) thin-wall sleeve 62 as shown in FIG. 3 is withdrawn to expose gripping elements 57 at distal portion 58 of the extension member. FIG. 6B depicts an elongate distal portion 20b of the embolic element 12 being disposed in the aneurysm sac 100 which has been caused by pushing the extension member 24 to and fro thereby causing the grip elements 57 to engage surface 33 of embolic element 12 and successively carry small axial lengths of element 12 distally into the aneurysm under fluoroscopic control. In this manner, any selected length of distal portion 20b of polymer element 12, for example from about 5 cm. to 200 cm. for a typical aneurysm, can be fed into the malformation. The selected length and volume of embolic element 12 thereby displaces blood 101 and occupies a selected (first) volume of the vascular malformation.

As can be seen in FIG. 6B, the volume of aneurysm 100 can be substantially occupied with the embolic element 12, depending on its flexibility, to accomplish a first aspect of the method of the invention. In effect, the embolic element 12 causes an initial partial mechanical occlusion of the aneurysm volume by implanting a selected volume of occlusive material (i.e., the entangled length of polymer element 12) within the aneurysm which displaces a similar volume of blood 101 and thereby slows blood flow through the aneurysm and pressure therein. Next, a second novel aspect of the method of the invention is practiced wherein electrical energy is controllably delivered to embolic element 12 to increase the volume of occlusive material within the aneurysm by adding a layer of coagulum 104 about the polymer embolic element 12 thereby occupying a second volume of the aneurysm.

Figure 6C:
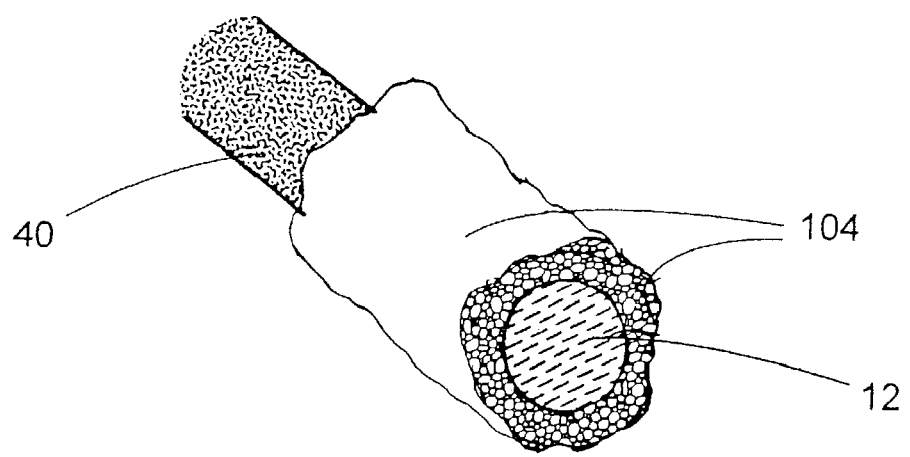
FIG. 6C is a graphic view of portion of a polymer embolic element with coagulum formed around the element by resistive heating of the metallic surface to increase the volume of occlusive material within a malformation.

More in particular, referring to FIGS. 6B & 6C, after the selected length of distal portion 20b of polymer element 12 is fed into aneurysm 100 under fluoroscopic control, the physician actuates the electrical source 50 via controller 55 to deliver electrical energy to electrode 44. The contact between electrode 44 and metallic surface 40 of polymer element 12 causes current flow along the metallic surface 40 of the entangled element and within the patient's body to a return electrode such as a ground pad in contact with the patient's body. The selected resistivity designed into the combination of metallic coating 40 and embolic element core 30, as described above, causes resistive heating of the element 12. The temperature of the surface 33 of the embolic element (as well as slight active ohmic heating of blood about the element 12) causes denatured blood products and coagulum to adhere about surface 33 of the embolic element. As depicted graphically in FIG. 6C, the thermally-induced coagulation of blood 101 causes a substantial layer of coagulum 104 to form around the embolic element 12 to thus provide a greater volume of occlusive material within the aneurysm 100. In a preferred mode of operation, the thermocouple 33 (see FIG. 3) together with feedback circuitry to the controller 55 are used to modulate power delivery to electrode 44 to maintain the embolic element at the catheter terminus at a pre-selected temperature level for a selected period of time. The method of invention maintains the surface temperature of embolic element 12 within a range of about 45° C. to 100° C. More preferably, the surface temperature of the embolic element is maintained within a range of about 65° C. to 90° C. to create the desired coagulum. This aspect of the method of the invention thus increases the volume of occlusive material within the vascular malformation to further mechanically reduce blood circulation within the defect. Thereafter, the occlusive material (embolic element and coagulative layer) within the aneurysm then rapidly will cause accumulation of platelets and other clotting factors about the occlusive material to complete the occlusion of the aneurysm volume as a result of the body's wound healing response to the occlusive material volume within the aneurysm 100.

In accomplishing the above-described method of the invention, the electrical energy delivery provided by source 50 and controller 55 can be in the radio frequency range and at a first power level ranging between about 1 watt and 50 watts. More preferably, the power level ranges between about 5 watts and 15 watts. It is proposed that current flow for about 5 seconds to 1200 seconds will cause the desired thickness of coagulative material to form around the embolic element 12 to assist in the mechanical occlusion of an aneurysm or other vascular defect. It should be appreciated that the duration of power delivery is a factor in creating a desired thickness of coagulative material on the embolic element. However, the process of causing the formation of a coagulative layer about the embolic element is essentially self-terminating, which adds to the safety of practicing the method of the invention. The method is self-terminating in the sense that as the coagulative layer builds to the desired selected thickness, the layer serves as an insulative layer and thereby prevents further denaturation of blood compositions (or ohmic heating of blood proximate to the embolic element.

The method of using an embolic element having a resistivity in the selected range described above has the advantage of preventing any possibility of creating energy densities ("hot spots") within the aneurysm wall that could perforate the aneurysm sac. The low power levels utilized in this method of the invention can easily cause resistive heating of the metallic surface coating 40 for coagulation purposes, but cannot cause significant localized current flows (i.e., energy densities) that could perforate a vessel wall, or create energy densities that could cause ohmic heating of collateral brain structure. Of particular importance, the thermally-induced coagulative process is effectively self-terminating since the temperature level at surface 33 of the metallic coating 40 will become insulated by the coagulum, thus preventing overheating of the interior or the aneurysm.

Figure 7:
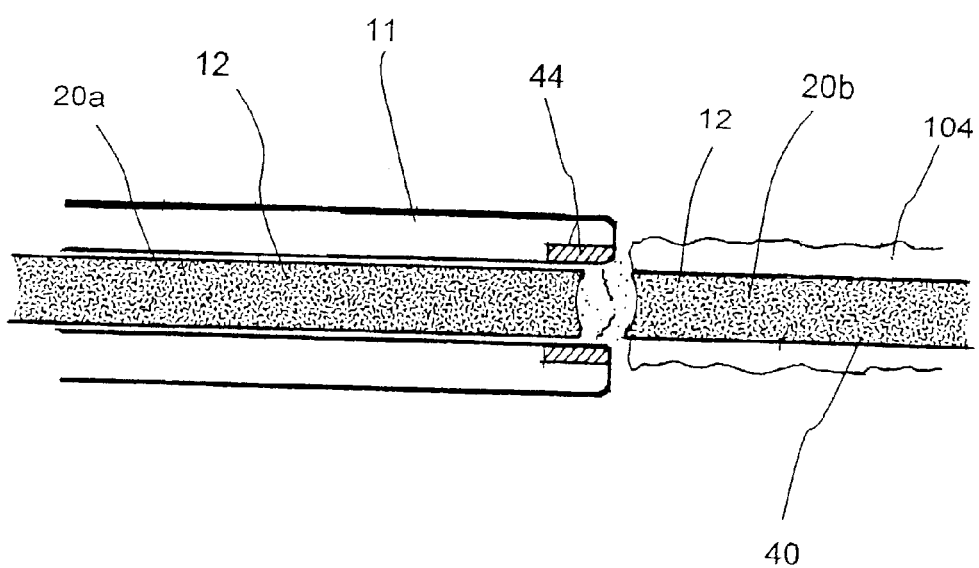
FIG. 7 is a graphic view of a manner of practicing a method of the invention in utilizing a selected level of electrical energy to divide the implanted embolic element from a proximal portion of the polymeric element still within the catheter sleeve.

FIG. 7 graphically illustrates the next step of the method of the invention that involves separation of the distal portion 20b of embolic element 12 entangled within aneurysm 102 (see FIG. 6B) from proximal portion 20a of embolic element 12 still within the catheter sleeve 10. In order to accomplish the separation of the embolic element 12 according to the invention, the physician actuates electrical source 50 via controller 55 to deliver current flow to electrode 44 that has a selected second (higher) power than the previously described power levels. As can be understood in FIG. 7, the insulative coagulum around the embolic element 12 will substantially prevent current flow at the second higher power level to course through the endovascular media, thus eliminating the possibility of high localized current densities. However, at the interface 107 between electrode 44 and metallic surface in contact with the electrode, the current flow will create a transient high energy density in and about metallic coating 40 and core 30 of element 12 to cause thermal melting of the polymer core to thereby divide the embolic element 12. To divide the embolic element, it is believed that a power level ranging between about 5 watts and 100 watts is suitable. More preferably, the power level is within the range of about 10 watts to 30 watts. It is believed that current flow for about 0.01 seconds to 20 seconds will divide the embolic element. Following the division of the implanted embolic element 12, the catheter 10 that carries the proximal portion 20a of the embolic element is withdrawn from the patient's vasculature.

The previously described means of dividing the embolic element with electrical energy has the particular advantage of allowing the physician to implant any desired length of the embolic element 12 within an aneurysm or other vascular defect. The physician simply can advance a length the polymer element into the defect under fluoroscopy until the entangled volume appears optimal, and then deliver electrical energy at the first and second power levels to (i) add coagulative volume to the occlusive material in the vascular defect, and then (ii) to separate the implanted embolic element 12 from the remainder of the element still within the catheter. This method of the invention, of course, can be practiced for implanting an embolic element without utilizing electrical energy to add a coagulative layer to the embolic element as described above.

In another embodiment of embolic element 12, the polymer or the metallic coating is formed in a coiled or curved shape and the material has a memory of such a curved shape. The flexible embolic element 12 then conforms to a generally linear configuration for feeding through a catheter sleeve. Upon deployment beyond the distal terminus of the catheter sleeve, the embolic element then will substantially assume its curved or coiled shape which will assist in its insertion into an aneurysm.

Figure 8:
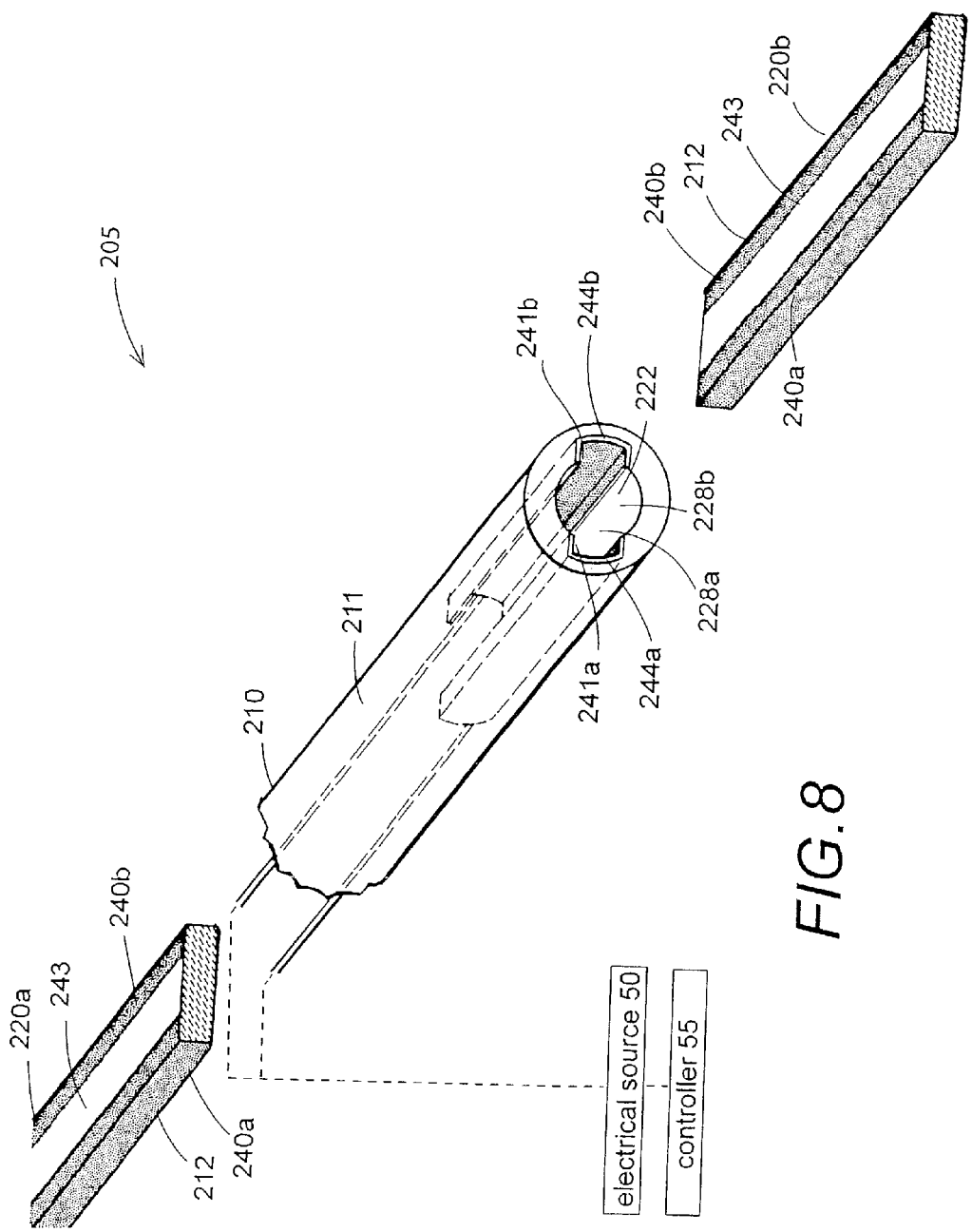
FIG. 8 is a cut-away view of the working end of Type "B" vaso-occlusive system showing a polymer embolic element with first and second spaced apart metallic coatings made in accordance with the principles of the invention.

2. Type "B" embodiment of vaso-occlusive system. FIG. 8 shows a cut-away view of a Type "B" catheter system 205 for occluding an aneurysm, other vascular defect or malformation or any targeted site within a patient's vasculature. The catheter system is similar to the previously described embodiment and has a proximal handle or manifold 8 coupled to an elongate microcatheter sleeve 210 that terminates in working end 211. As can be seen in FIG. 8, this system comprises a metallic-coated elongate member 212 that can be passed axially through the a cooperating bore 222 in the microcatheter sleeve 210. This Type "B" system differs from the previously disclosed system in that the flexible continuous embolic member 212 (that defines proximal portion 220a and distal thread portion 220b) functions in two alternative manners: (i) the flattened embolic member 212 is substantially stiffened to allow it to be pushed outward from a handle end 8 of the catheter sleeve without requiring a pushing member or extension member as described above, and (ii) the polymer embolic member 212 carries first and second spaced apart metallic coating portions to act as resistive elements and to further act as a bi-polar delivery system to perform alternative methods of the invention in creating coagulative material and in dividing the polymer embolic member 212 after implantation in a vascular malformation.

In this exemplary Type "B" system embodiment, the internal bore 222 is shaped to receive the flattened embolic thread member 212 in a rectangular shaped bore portion indicated at 228a. Additionally, the catheter sleeve is adapted to slide over a round guidewire (not shown) that is accommodated by the round shape bore portion 228b. In this embodiment, the embolic thread member 212 again has a body core 230 of a continuous length of a flexible polymeric filament. The polymer embolic member 212 again carries a radio-opaque composition.

As can be seen in FIG. 8, this alternative embodiment of embolic member 212 carries first and second opposing thin-wall metallic coating portions 240a and 240b that extend the length of the embolic member 212. The metallic coating in this embodiment again has a selected resistivity to current flow that ranges from about 1 ohm to 500 ohms per 10 cm. length, although a lesser resistivity also is functional for some methods of the invention. For example, the opposing metallic coating portions 240a and 240b can act as bi-polar electrodes as will be described below. In such an application, the first and second metallic portions 240a and 240b extends along first and second sides 241a and 241b of the entire length of the embolic member 212. It can be seen that these first and second metallic surfaces define a center-to-center dimension and can act as bi-polar electrodes, since the surface portions are spaced apart on either side of a medial non-metallic surface portion indicated at 243.

FIG. 8 further illustrates that working end 211 of catheter sleeve 210 carries spaced apart first and second conductive electrodes 244A and 244B on either side of bore portion 228a that carries embolic member 212. The electrodes 244A and 244B are coupled to electrical leads 246a and 246b in wall 248 that extend to electrical source 50 and controller 55. As can be understood by viewing FIG. 8, the elongate polymer member 212 is substantially stiff so that it can be pushed distally from bore portion 228a from the handle end of the catheter, and the electrodes 244A and 244B will always be in contact with the respective metallic surface portions 240a and 240b of the polymer element 212. Alternatively, the embolic member can be pushed distally by an extension member as described previously.

The manner of using catheter system 205 to perform the methods of occluding a cerebral aneurysm 100 can be easily described, still referring to FIG. 8. The elongate polymer member 212 is passed through the catheter sleeve 210 and thereby fed into the aneurysm 100 similar to the graphic representation of FIG. 6B. Thereafter, a guidewire (if used) is withdrawn from the catheter passageway 228b. Thus, the aneurysm sac can be substantially occupied with embolic member 212 to partially mechanically occlude the aneurysm volume.

Next, the physician actuates electrical source 50 via controller 55 to deliver electrical energy to common polarity electrodes 244A and 244B. The contact between electrodes 244A and 244B and the metallic surface portions 240a and 240b of embolic member 212 causes current flow along the metallic surfaces of the entangled member in cooperation with a return electrode such as a ground pad. The selected resistivity of the metallic surface portions 240a and 240b of polymer element 212 then will coagulate blood about the surface of the embolic member 212, generally as described previously to add to the volume of implanted occlusive material.

In a more preferred method of operation, the electrical source 50 and system 205 is provided with circuitry that allows controller 55 to programmably deliver bi-polar Rf current at a first power level to electrodes 244A and 244B which are in contact with the opposing metallic surface portions 240a and 240b of polymer member 212 to cause current flow between the metallic surface portions 240a and 240b. This manner of bi-polar current flow is advantageous since it will not cause high current densities in any endovascular media that might then threaten perforation of the aneurysm wall. Such bi-polar flow thus will rapidly cause a coagulative layer on the embolic member (generally between the metallic surface portions 240a and 240b) to thereby add to the volume of occlusive material within the aneurysm. In using the paired metallic surface portions 240a and 240b in such a bi-polar energy delivery modality, the metallic coatings may provide any lesser resistivity to current flow for performing the method of the invention.

In another energy delivery modality, the controller may sequence delivery of mono-polar Rf current to the working end 211 in cooperation with a ground pad and bi-polar flow between the paired metallic surface portions 240a and 240b to cause coagulum to form about the embolic member 212. The system further may use a thermocouple (not shown) and feedback circuitry as described above to maintain the surface of the embolic member within the desired temperature range as described above.

The use of the paired metallic surface portions 240a and 240b in a bi-polar mode is particularly adapted for use in the next step of the method of the invention that involves separation of the distal portion 220b of embolic member 212 entangled within aneurysm 102 (cf FIG. 6B) from proximal portion 220a still within catheter sleeve 210. In using this embodiment, the physician actuates electrical source 50 via controller 55 to deliver bi-polar Rf current flow between electrodes 244A and 244B at a selected second (higher) power level than used in the coagulation modality. In this case, the second power level causes the core 230 of embolic member 212 to resemble a fuse as the current courses between the electrodes to thus divide embolic member 212 at the distal termination 226 of the catheter sleeve. It is believed that the method of using bi-polar Rf current flow between paired electrodes will allow separation of the embolic member 212 within a range of about 0.1 to 10 seconds. Again, this embodiment of the invention then allows any suitable length of embolic member 212 to be introduced into the aneurysm—and then separated at the catheter end.

In another Type "B" embodiment, the emboli member may have a transverse section in the shape of a "C" (not shown) to partially wrap around a guidewire or a pusher member (see FIG. 3). It can be easily understood that such a cross-sectional shape would allow the "C" shape to function in the fashion of rapid-exchange catheter systems as are known in the art to insert over a guidewire. Further, this embodiment would allow bi-polar electrode surfaces on opposing and spaced apart inner and outer surfaces of the embolic member to otherwise function as described above.

Figure 9:
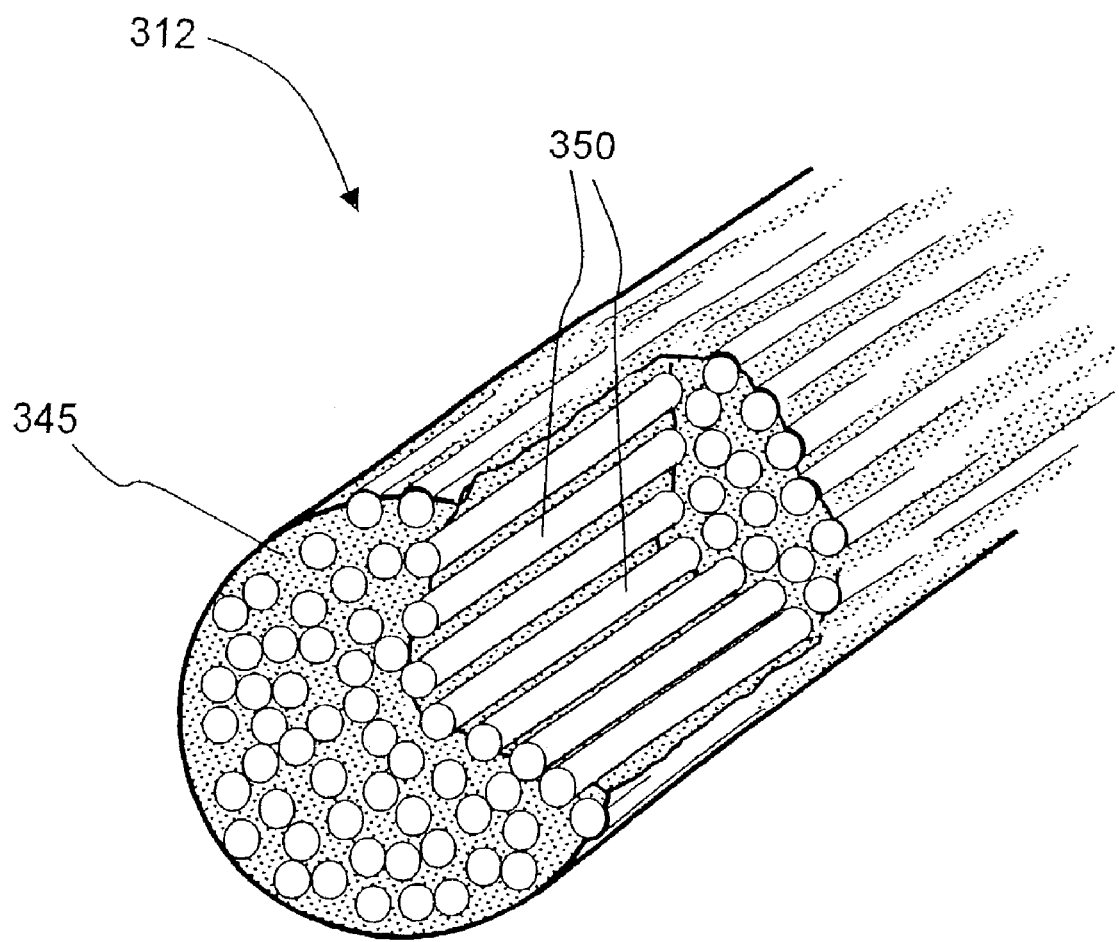
FIG. 9 is a sectional view of an embolic element of a Type "C" vaso-occlusive system wherein the embolic element comprises a matrix of a polymer with conductive microfilaments embedded therein.
Figure 10:
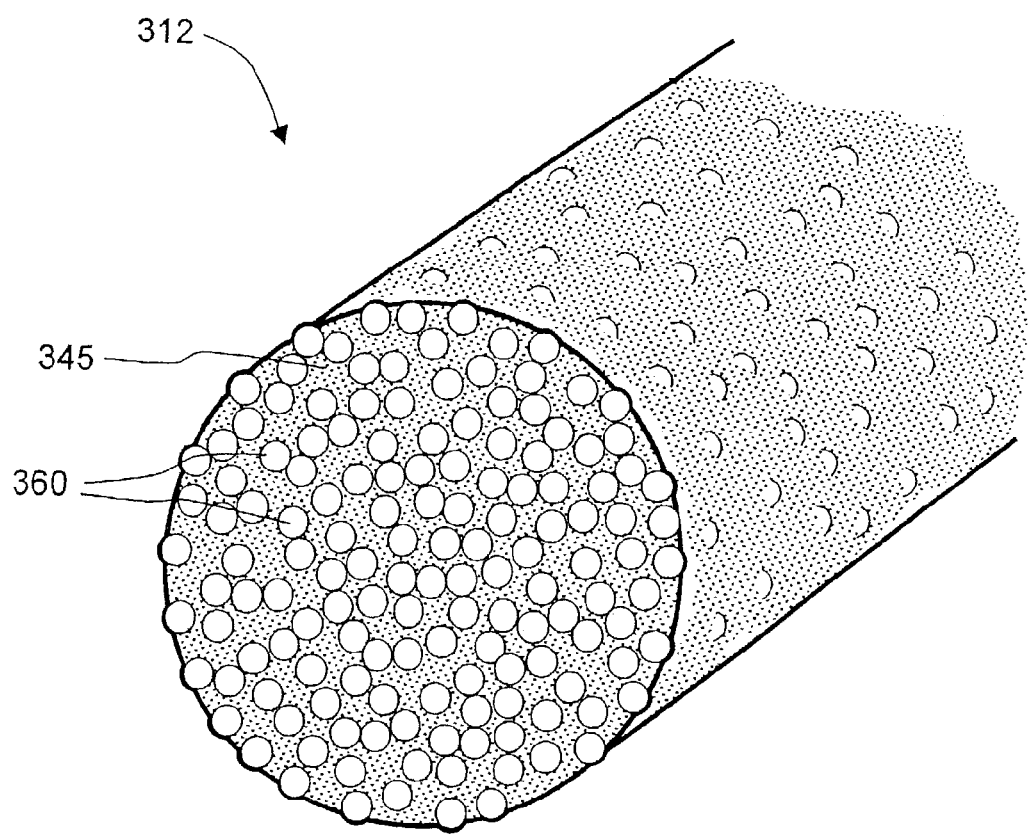
FIG. 10 is a sectional view of an alternative embolic element of a Type "C" vaso-occlusive system wherein the embolic element comprises a matrix of a polymer with conductive particles distributed therein.

3. Type "C" vaso-occlusive system. This alternative Type "C" system uses a catheter sleeve as described in the Type "A" embodiment above. This system differs only in the construction of elongate embolic member 312 shown in FIGS. 9 and 10. The flexible continuously extruded embolic member 312 again comprises a substantially polymer core together with a conductive component that provides the member with a specified resistivity. In one alternative embodiment of Type "C" embolic member shown in FIG. 9, the member 312 comprises a polymer matrix 345 that is co-extruded with micro-filaments 350 of any suitable conductive material embedded therein, such as tungsten, stainless steel or carbon fiber. The micro-filaments 350 can be partially exposed at the surface of the member to contact the electrode arrangement carried at the distal termination of the catheter sleeve. In another alternative Type "C" embolic member shown in FIG. 10, the member 312 comprises a polymer matrix 345 with embedded particles 360 of any suitable conductive material to thereby provide the resistivity specified above. The polymer conductive-resistive matrix of embolic member 312 functions as a fuse to divide the embolic member at the distal end of a catheter as described in the Type "A" embodiment.

Figure 11:
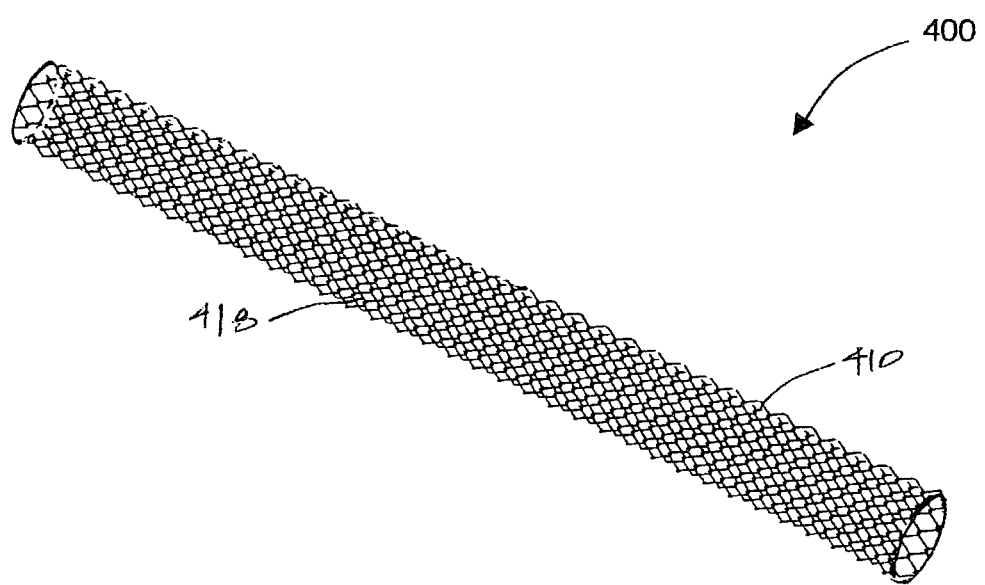
FIG. 11 is a perspective view of a Type "D" vaso-occlusive system that comprises a polymer sleeve having a mesh-like wall of woven filaments having a specified resistivity.
Figure 12:
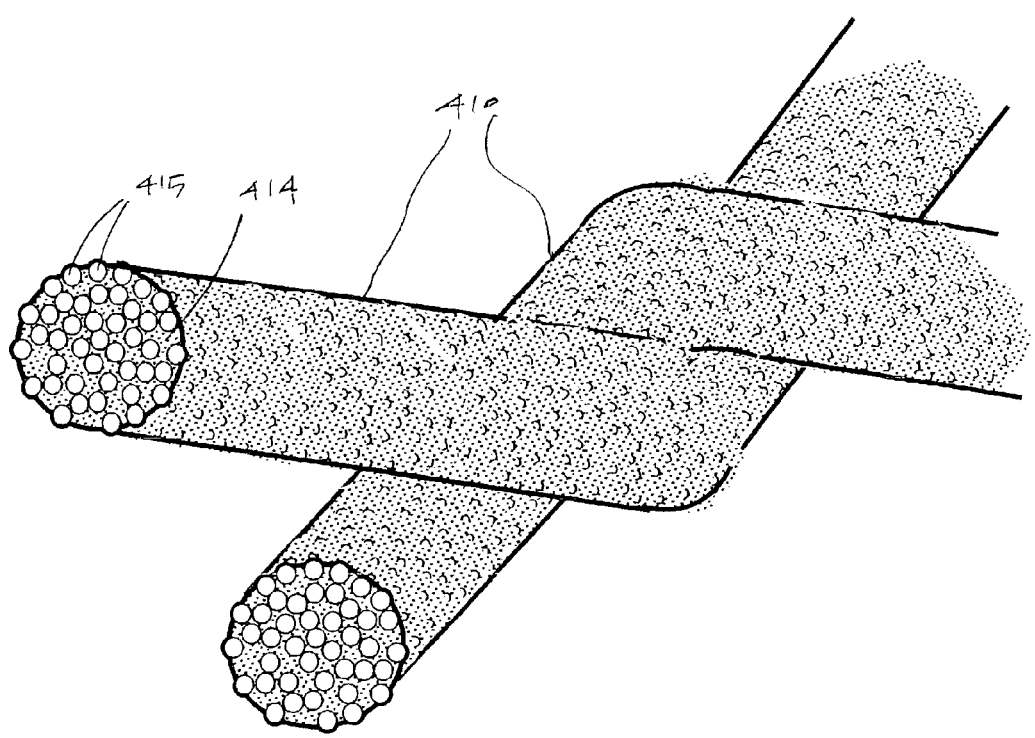
FIG. 12 is an enlarged view of the woven filaments of FIG. 11 depicting conductive particles therein.
Figure 13A:
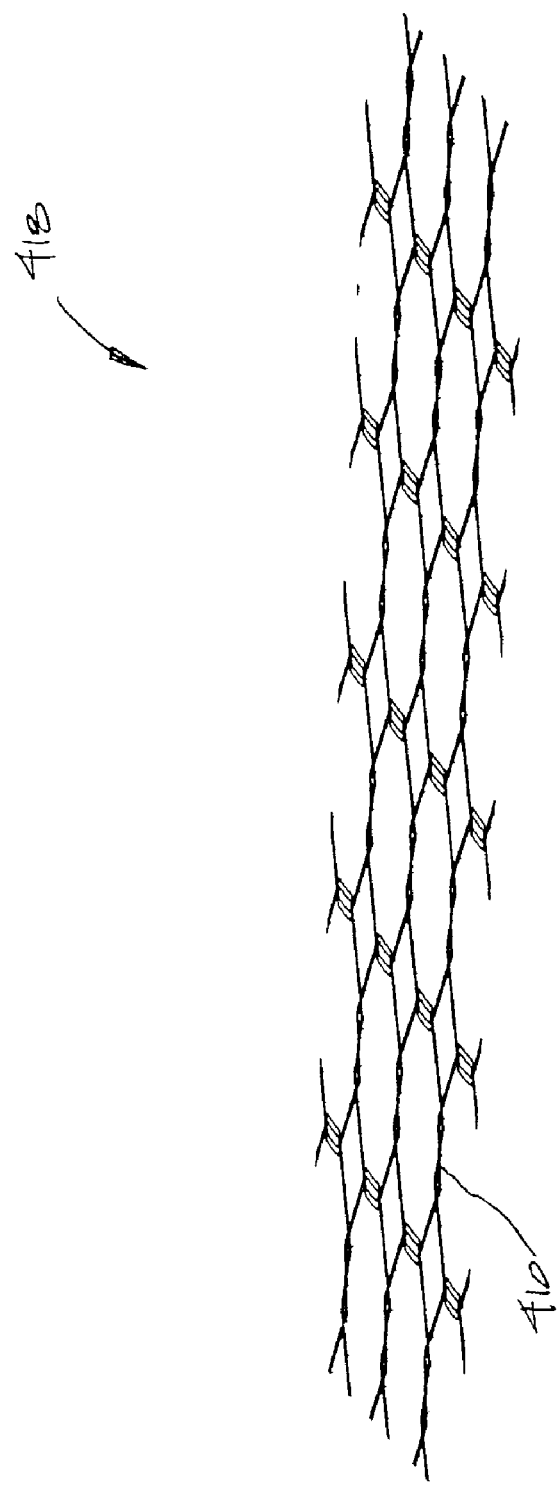
FIGS. 13A–13B are an enlarged views of the mesh-like wall of woven filaments of FIG. 11 showing non-expanded and expanded positions.
Figure 13B:
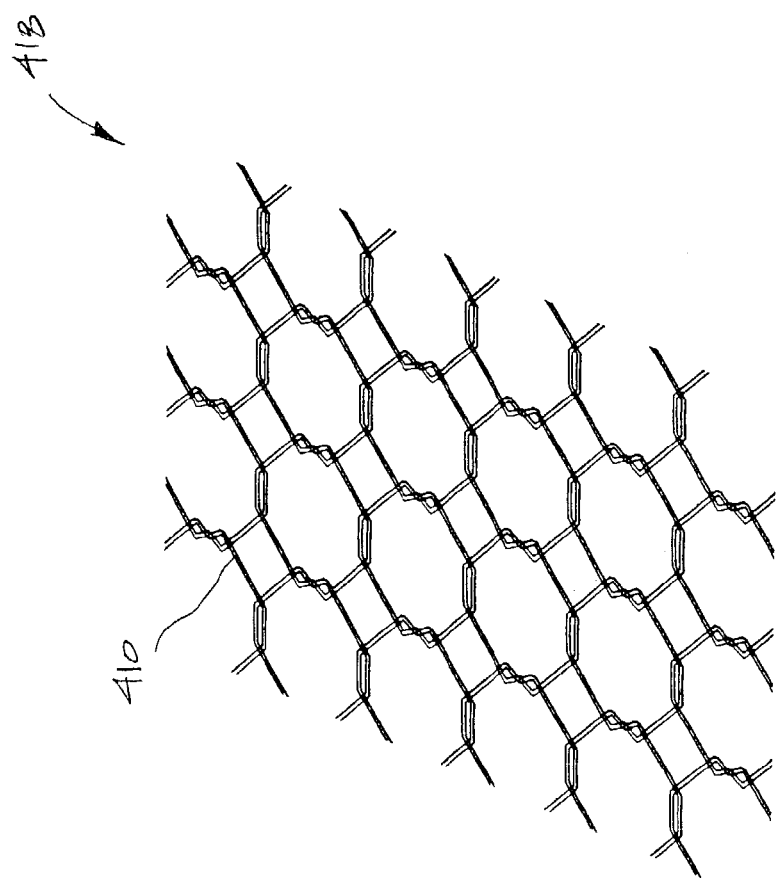

4. Type "D" embodiment of vaso-occlusive system. Referring to FIG. 11, the Type "D" vaso-occlusive system comprises a tubular sleeve 400 that is assembled or woven from a polymer filament 410 of the type that was described previously (see FIG. 10). The filament preferably is of the type illustrated (not-to-scale) in FIGS. 11–12 wherein the filament 410 comprises a first polymer portion 414 and a conductive portion 415. In one embodiment, the conductive portion 415 can comprise conductive particles such as carbon in a size ranging from about 1 nm to 10 microns. The conductive portion 415 alternatively can be any other conductive particle or filament of gold, silver or the like. The polymer filament 410 is then woven into a sleeve as depicted in FIG. 11 that can be moved between a first contracted cross-section and a second expanded cross-section. FIGS. 13A–13B depicts that woven wall structure 418 of the sleeve 400 as it is expanded from the first position (FIG. 13A) to the second position (FIG. 13B). The polymer filament 410 can have any suitable diameter ranging from about 0.0005" to 0.005". The polymer filament 410 also can of the type described in the Type "A" embodiment above wherein the polymer filament is made conductive by means of a very thin metallic coating.

The diameter of the filament 410 can be any suitable dimension to provide a sleeve 400 with a selected overall diameter for adhering to the walls of a blood vessel. In use, the filament 410 is adapted to receive electrical energy from source 50 wherein the conductive polymer conductive-resistive matrix is designed with a specified resistivity within a particular temperature range that will heat the filament to a selected temperature. The selected temperature is adapted to fuse the filaments of the sleeve to the vessel wall, as will be described next. The characteristics and features of the conductive polymer matrix corresponding to the invention are described in detail in co-pending Provisional U.S. patent application Ser. No. 60/366,992 filed Mar. 20, 2002 (Docket No. SRX-015) titled *Electrosurgical Instrument and Method of Use*, which is incorporated herein by reference. In co-pending Ser. No. 60/366,992, a conductive polymer matrix is disclosed for controllably delivering energy to tissue for purpose of tissue welding or tissue sealing, which is somewhat similar to the objectives of the present invention. The method of the present invention involves bonding a filament to tissue with the controlled application of electrical energy, which can rely on the positive temperature coefficient characteristics described in detail in co-pending Ser. No. 60/366,992.

Figure 14A:
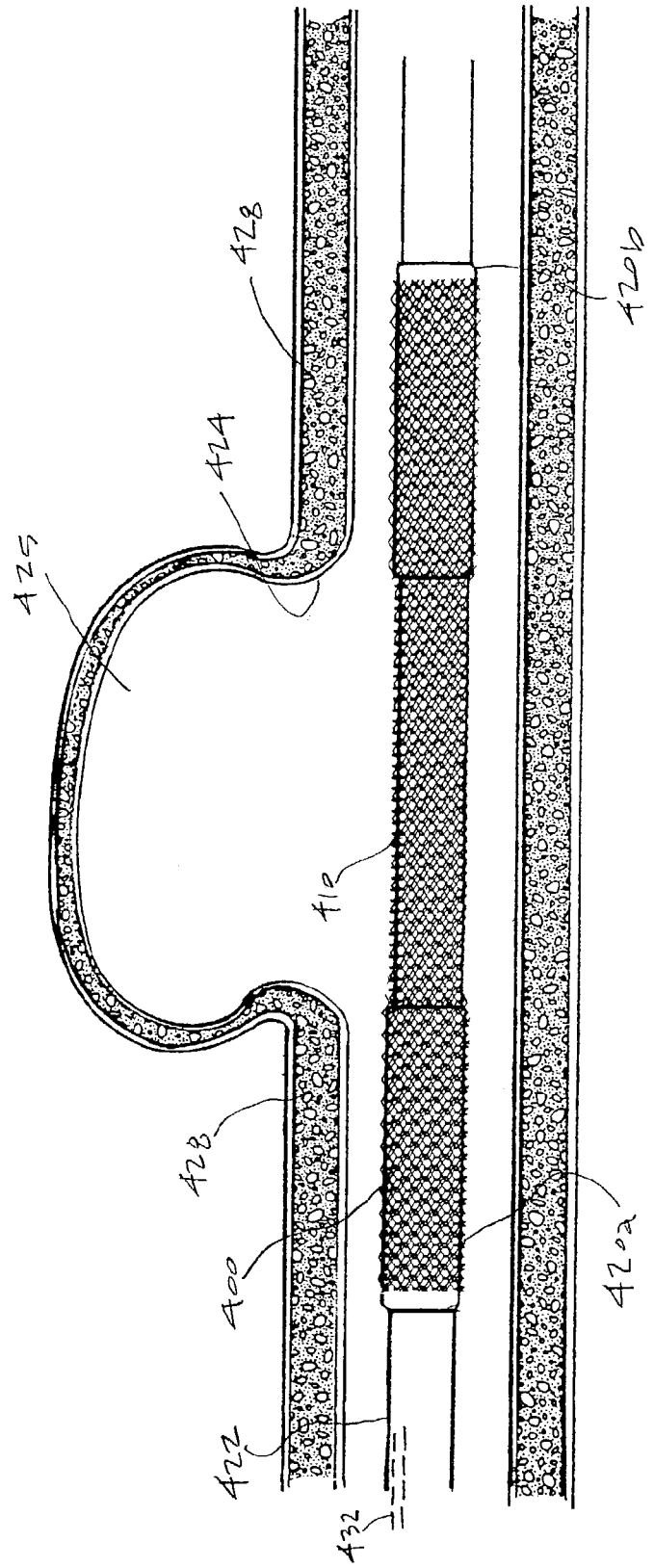
Figure 14B:
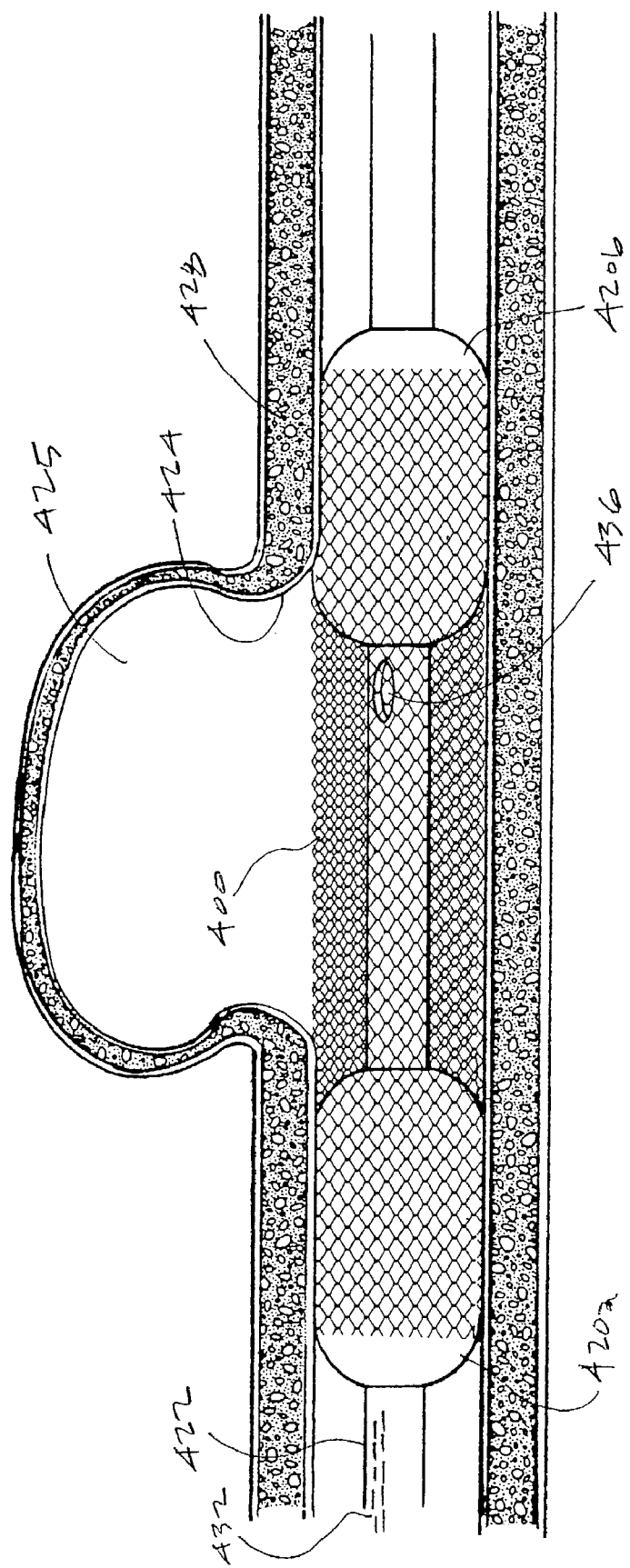
Figure 14C:
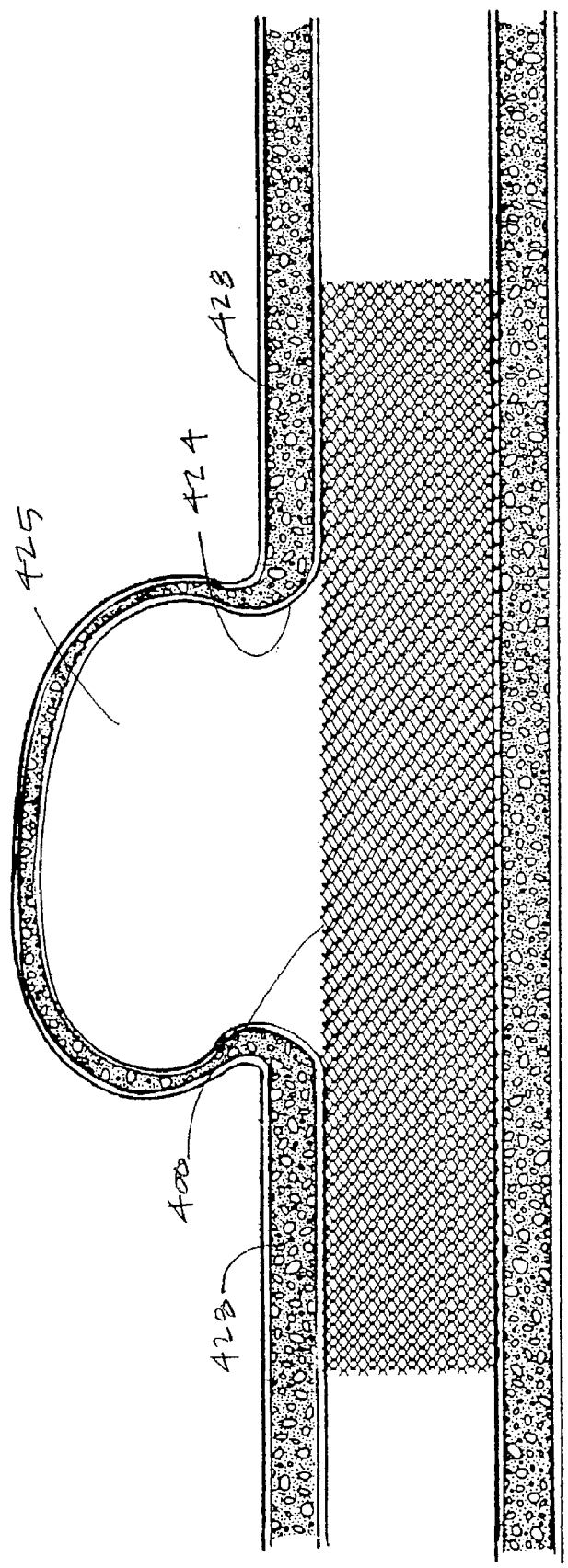

FIGS. 14A–14C next graphically depict the manner of using the polymer matrix sleeve 400 to treat a vascular malformation. The polymer filament sleeve 400 of FIG. 11 is particularly designed for treatment of wide-neck aneurysms, some-times referred to as "top-hat" aneurysms. Such malformations are often difficult to treat with embolic coils or other embolic filler materials since the vaso-occlusive materials may not be stable within the aneurysm sac. The polymer filament sleeve 400 is thus adapted to extend across the neck of aneurysm and thereafter be instantaneously fused to the vessel wall with the application of electrical energy. The filament sleeve 400 differs markedly from a conventional stent since the polymer sleeve is flexible, has an extremely thin wall dimension and becomes fused to the vessel wall for maintaining its position. In contrast, a stent is not flexible which leads to constant trauma to the vessel wall as it slightly changes in dimension as the vessel wall expands and contracts during the pulses of blood flow therethrough. Further, the stent remains in position only because of its expanded strength that pushes against the vessel wall.

FIG. 14A shows the polymer filament sleeve 400 is an assembly being disposed over first and second expandable balloons 420a and 420b at the working end of an elongate flexible introducer member 422. The sleeve 400 also can be carried over a single balloon member or any other type of expansion structure. In FIG. 14A, the sleeve 400 is positioned across the large open neck 424 of an exemplary aneurysm 425 in vessel wall 428. The introducer member 422 and at least one balloon can carry any suitable markings for cooperating with an imaging system.

FIG. 14B next illustrates the expansion of the balloons 420a and 420b that presses the woven wall structure 418 of the sleeve 400 against the walls 428 of the vessel. At least one inflation lumen 432 extends through the introducer member 422 to a pressure source as is known in the art.

Still referring to FIG. 14B, after the sleeve 400 is in an expanded or deployed position against the vessel walls, the electrical source 50 is actuated to deliver electrical current to the conductive filaments 410 of sleeve 400. The very fine filaments 410 can be elevated to a selected temperature of between about 60° C. and 90° C. for an interval ranging from about 0.01 second to 5.0 seconds which will fuse the filaments to the vessel wall 428. Preferably, the time interval of energy delivery is less that about 1.0 second. The very rapid energy delivery to the small cross-section filaments will prevent any substantial damage to the vessel walls.

FIG. 14C illustrates the sleeve 400 deployed and fused to the vessel walls after collapse of the balloons and withdrawal of the introducer member. The use of the polymer sleeve 400 alone can serve as a complete treatment for some types of aneurysms as the wall 418 of the sleeve that extends across the neck 424 of the aneurysm will cause a significant reduction in blood flow into and around the aneurysm which will lead to thrombosis in the aneurysm sac 425.

It should be appreciated that another sleeve 400 (not shown) can have a less porous central wall portion that extends across the neck 424 of the aneurysm to more effectively prevent blood flow into the aneurysm sac 425.

In another manner of practicing the invention, an embolic material may be introduced into the aneurysm sac 425 following deployment of the polymer sleeve 400 across the neck 424 of the aneurysm. Thus, the polymer sleeve 400 then can function as a mesh to retain the embolic material within a wide-neck aneurysm. The embolic material can be of any type known in the art, such as embolic coils, foams or liquid agents that can be cured or solidified within the aneurysm sac 425. FIG. 14B illustrates that the introducer 422 itself can have a port 436 for introducing embolic material into the aneurysm while the balloons are expanded and stabilizing the sleeve 400 across the neck 424 of the aneurysm.

The electrode connection between the introducer 422 and the sleeve 400 can be on the surfaces of the balloons or within the distal end of a bore that extends about the proximal end of the polymer sleeve 400. The polymer sleeve 400 thus can be an independent member in contact with an electrode or the sleeve can detach from a connection to the introducer member by the fuse-type means described previously. The system can operate with any type and location of return electrode.

Figure 15:
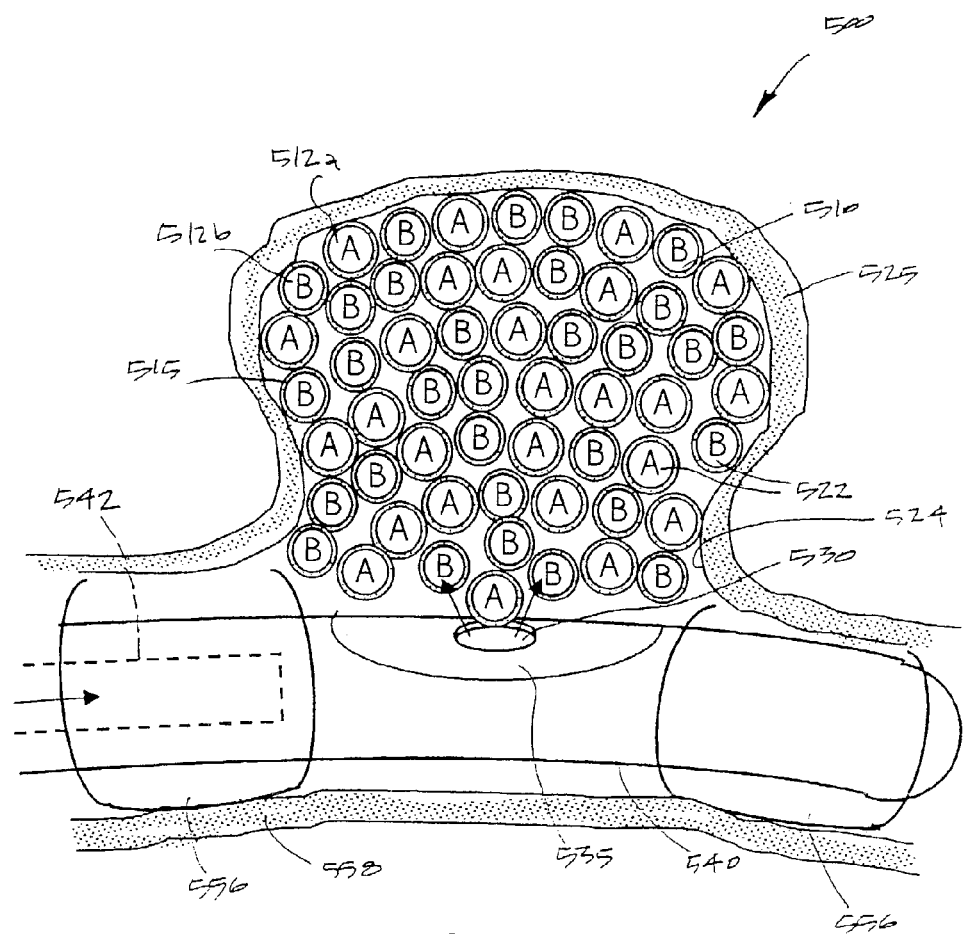
FIG. 15 is a schematic view of a Type "E" vaso-occlusive system and first step in it method of use wherein a catheter working end introduces a binary media of microspheres with sacrificial shells into an aneurysm sac.

5. Type "E" vaso-occlusive system. FIG. 15 provides a schematic illustration of an exemplary Type "E" vaso-occlusive system 500 that is adapted to fill an aneurysm sac with novel media 510 corresponding to the invention that can be altered from a first flowable state to a second more solidified state. The system and media 510 are directly related to the conductive-resistive polymer matrix described in the Types "C" and "D" embodiments above and in co-pending Provisional U.S. patent application Ser. No. 60/366,992 filed Mar. 20, 2002 titled *Electrosurgical Instrument and Method of Use*, referenced above.

In FIG. 15, the system of the invention is shown schematically wherein a binary system of biocompatible agents are encapsulated in microspheres 512a and 512b. The microspheres have an exterior sacrificial shell portion indicated at 515 that is of a conductive matrix material as described previously. The interior or cores 522 of the microspheres 512 comprise either a first or second composition (indicated at "A" or "B" in FIG. 15) that when mixed together cause a polymerization process between the compositions that will alter the media 510 from a flowable media to a substantially non-flowable media, e.g., a solid or stiff gel-like material. Thus, the media 510 in its flowable state—with first and second types of microspheres therein—can be introduced into an aneurysm from an opening in the distal termination of a catheter, or from a port 530 in the side of the catheter's working end. Any type of pusher mechanism can be used to expel the flowable media 510 from the catheter. Preferably, the flowable media 510 carries radio-opaque materials or any other material that can cooperate with an imaging system to allow the physician the ability to view the introduction of the media into an aneurysm 525 (FIG. 15).

The sacrificial shell portions 515 of the microspheres can be of a degradable material similar to materials described previously that have conductive particles distributed therein. In one embodiment, the shell material 515 carries particles that can generally be described as "radiosensitive" in that they respond to electromagnetic energy of a selected frequency. Thus, the catheter corresponding to the invention can carry energy deliver means (alternatively termed degrading means) for reducing, degrading, disintegrating or otherwise fracturing sacrificial shell portions 515 of the microspheres. In one embodiment, the sacrificial shell can be a wax or lipid with radiosensitive particles therein that can be elevated in temperature (i) by resistive heating due to current flow from an electrode 535 on the catheter working end or (ii) by inductive heating from an emitter electrode as is known in the art.

Thus, the invention provides a vaso-occlusive system that comprises a flowable media 510 that carries a volume of microspheres of first and second types, wherein each type of microsphere has a sacrificial shell that surrounds an interior core portion. The core portions, when allowed to interact, form a binary system for polymerizing the media into a non-flowable gel or a solid.

Now turning to FIG. 15, the distal working end 540 of a catheter is shown schematically as being introduced to the region opposing the neck 524 of an aneurysm 525. A pusher 542 is used to expel a volume of media 510 from the port 530 which is directed into the aneurysm. The axial movement and angular rotation of the catheter is assisted by suitable markings on the catheter that cooperate with an imaging system. During navigation of the catheter, the port 530 can be maintained in a closed state by a slidable cover, or a by burstable film or the like. The volume of media 510 in FIG. 15 is illustrated for convenience with "A" and "B" particles 512a and 512b that are grossly out of scale. In practice, the microspheres can have a dimension across a principal axis thereof ranging between about 10 nanometers and 100 microns. More preferably, the microspheres have a dimension across a principal axis ranging between about 100 nanometers and 50 microns. FIG. 15 further shows that the catheter working end 540 carries an optional balloon system 556 for engaging the walls 558 of the blood vessel to insure that all of the media 510 is directed into the aneurysm sac.

Figure 16:
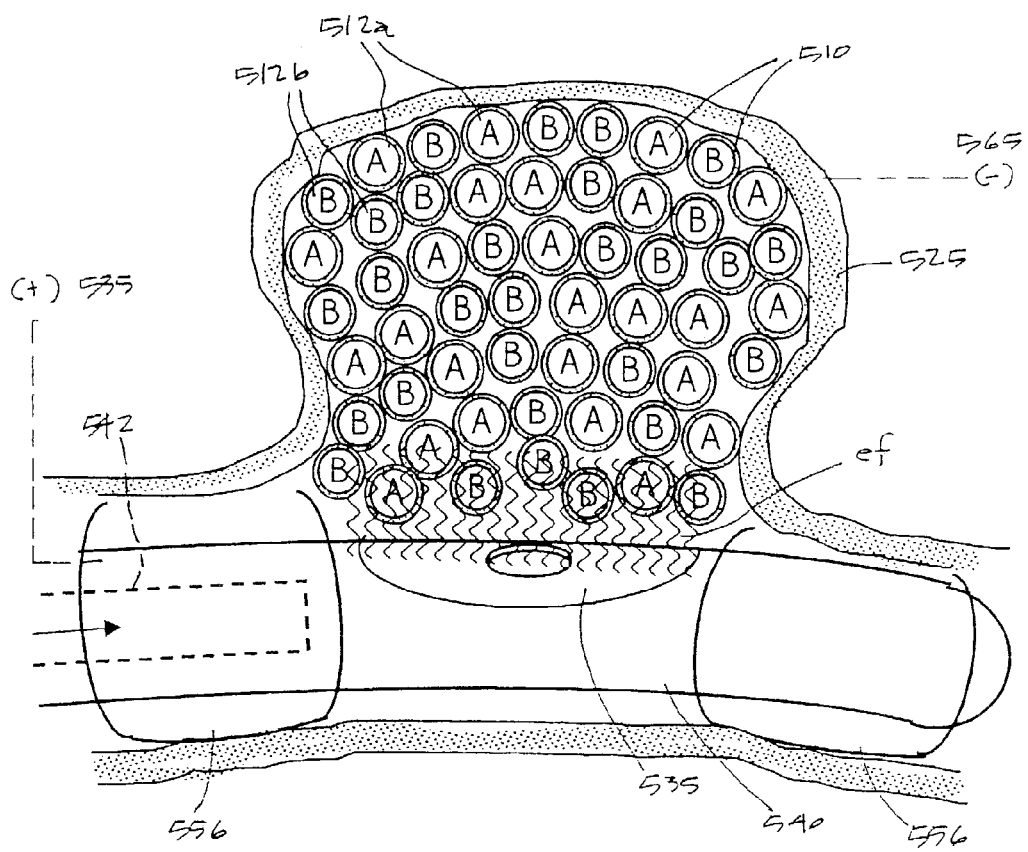
FIG. 16 is a schematic view of another step in utilizing the Type "E" vaso-occlusive system to practice the method of the invention.

Referring next to FIG. 16, the distal working end 540 is illustrating delivering energy to the volume of media 510 contained in the aneurysm sac 525. The delivering of energy is indicated by energy field of that in this embodiment consists of electrical current between first polarity (+) electrode 535 and a return (−) electrode 565 that can be a ground pad as is known in the art. This step of the method will resistively heat the sacrificial shell portions 515 of the microspheres until they degrade or melt.

Figure 17:
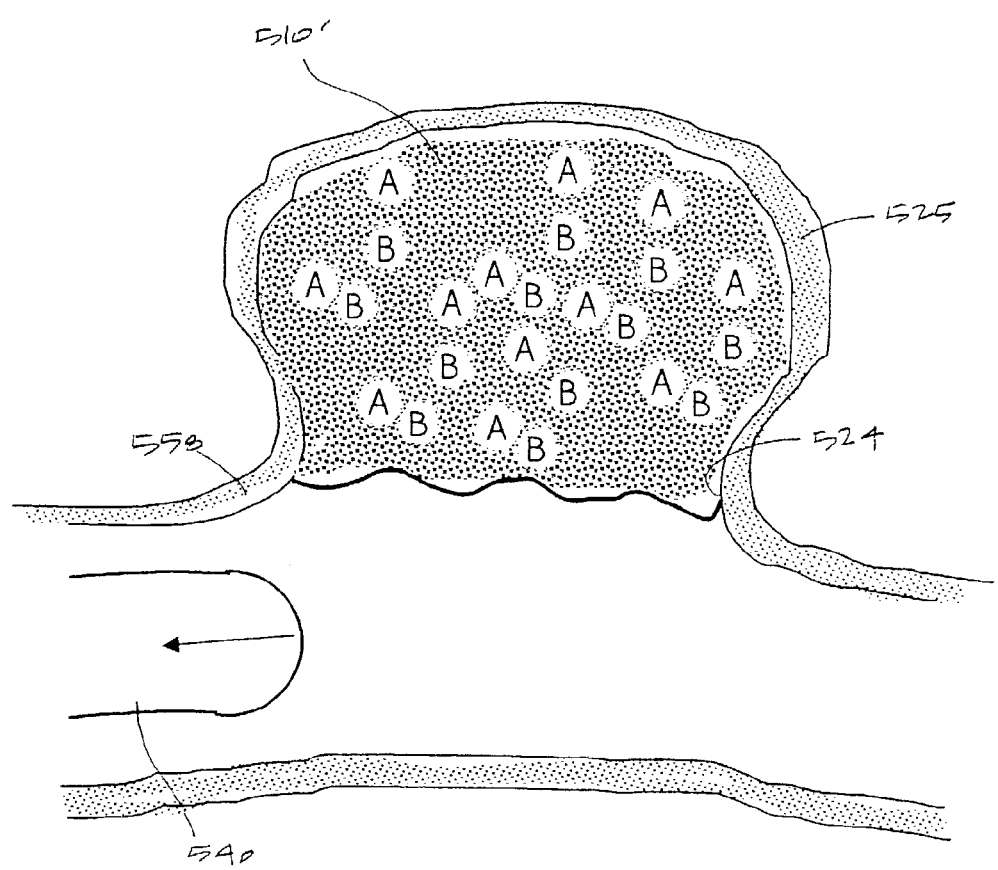
FIG. 17 is a view of a final step in practicing a method of the invention with the system of FIGS. 15–16.

FIG. 17 next schematically illustrates the interaction of the released "A" and "B" compositions 512a and 512b from the cores of the microspheres that creates a uniform non-flowable volume of media 510' that occludes the aneurysm sac. FIG. 17 further illustrates the steps of collapsing the balloon member 556 and withdrawing the catheter from the targeted site.

In another embodiment (not shown), the catheter working end 540 can carry opposing polarity spaced apart first and second electrodes for delivering current to the conductive sacrificial shell portions 515 of the media in what can be described as a bi-polar electrode arrangement.

In another embodiment (not shown), the energy emitter can be the terminal end of an optic fiber coupled to a light source, such as a laser. The sacrificial shell portions 515 of the media can carry a chromophore for cooperating with a selected wavelength of the light source to again thermally degrade the sacrificial shell portions 515 of the microspheres. In all other respects, the system for occluding a vascular malformation would be the same.

Those skilled in the art will appreciate that the exemplary embodiments and descriptions of the invention herein are merely illustrative of the invention as a whole. Specific features of the invention may be shown in some figures and not in others, and this is for convenience only and any feature may be combined with another in accordance with the invention. While the principles of the invention have been made clear in the exemplary embodiments, it will be obvious to those skilled in the art that modifications of the structure, arrangement, proportions, elements, and materials may be utilized in the practice of the invention, and otherwise, which are particularly adapted to specific environments and operative requirements without departing from the principles of the invention. The appended claims are intended to cover and embrace any and all such modifications, with the limits only being the true purview, spirit and scope of the invention.

What is claimed is:

1. A vaso-occlusive system, comprising:
   a catheter having a distal working end with an interior chamber;
   a volume of microspheres carried in said interior chamber, each microsphere having a sacrificial shell portion that surrounds an interior core portion;
   the core portions of the microspheres comprising either a first or second polymerizing composition, wherein interaction of said first and second compositions causes a polymerization process to thereby create a substantially solid volume; and
   energy delivery means within the catheter for causing removal of said sacrificial shells of said volume of microspheres.

2. The vaso-occlusive system of claim 1 wherein said sacrificial shell portion comprises a conductive polymer.

3. The vaso-occlusive system of claim 1 wherein said sacrificial shell portion has a specified resistivity that causes its disintegration upon a selected level of electrical current flow therethrough.

4. The vaso-occlusive system of claim 1 wherein the microspheres have a dimension across a principal axis thereof ranging between about 10 nanometers and 100 microns.

5. The vaso-occlusive system of claim 1 wherein the microspheres have a dimension across a principal axis thereof ranging between about 100 nanometers and 50 microns.

6. The vaso-occlusive system of claim 1 wherein said sacrificial shell portion has a specified resistivity that ranging between about 0.1 ohm/cm. to about 50 ohms/cm.

7. The vaso-occlusive system of claim 1 wherein said sacrificial shell portion has a specified resistivity that ranging between about 0.1 ohm/cm. to about 10 ohms/cm.

8. The vaso-occlusive system of claim 1 wherein said sacrificial shell portion comprises a polymer carrying a selected chromophore.

9. The vaso-occlusive system of claim 1 wherein energy delivery means within the catheter comprises at least one electrode coupled to an electrical source.

10. The vaso-occlusive system of claim 1 wherein energy delivery means within the catheter comprises an emitter coupled to a light source.

11. A method of treating a vascular malformation at a targeted site within a patient's vasculature, comprising the steps of:
   (a) navigating a catheter working end to the targeted site in the patient's vasculature;
   (b) introducing flowable media from the catheter working end into the vascular malformation wherein said flowable media carries a volume of microspheres, each microsphere having a sacrificial shell portion that surrounds an interior core portion of either a first or second polymerizing composition that upon interaction cause a polymerization process;
   (c) activating energy delivery means carried at the catheter working end to cause disintegration of the sacrificial shell portions of the microspheres; and
   (d) causing interaction of the first and second polymerizing compositions thereby altering the flowable media to a substantially solid media volume to provide occlusive media.

12. The method of claim 11 wherein the activating step delivers electrical energy to the sacrificial shell portions of the microspheres.

13. The method of claim 11 wherein the activating step delivers electrical energy from a single polarity electrode carried in the catheter working end.

14. The method of claim 11 wherein the activating step delivers electrical energy between opposing polarity electrodes carried in the catheter working end.

15. The method of claim 11 wherein the activating step causes the thermal breakdown of said sacrificial shell portions of the microspheres.

16. The method of claim 11 wherein the activating step delivers light energy to the sacrificial shell portions of the microspheres.

17. A vaso-occlusive system, comprising:
   a fluid media carrying a volume of microspheres of first and second types,
   the first type of microsphere having a sacrificial shell portion that surrounds an interior core of a first composition;

the second type of microsphere having a sacrificial shell portion that surrounds an interior core of a second composition; and wherein interaction of said first and second compositions causes a polymerization of the volume of fluid media.

18. The vaso-occlusive system of claim 17 further comprising degrading means for degrading said sacrificial shell portions of the microspheres.

19. The vaso-occlusive system of claim 17 wherein the degrading means comprises an electrical energy source that cooperates with radiosensitive compositions in said sacrificial shell portions of the microspheres to thermally degrade said sacrificial shell portions.

20. The vaso-occlusive system of claim 17 wherein the degrading means comprises a light energy source that cooperates with chromophores compositions in said sacrificial shell portions of the microspheres to thermally degrade said sacrificial shell portions.

* * * * *